(12) United States Patent
Harris et al.

(10) Patent No.: US 9,604,999 B2
(45) Date of Patent: Mar. 28, 2017

(54) COMPOUNDS AND USES THEREOF FOR THE MODULATION OF HEMOGLOBIN

(71) Applicant: Global Blood Therapeutics, Inc., South San Francisco, CA (US)

(72) Inventors: Jason R. Harris, South San Francisco, CA (US); Qing Xu, South San Francisco, CA (US); Zhe Li, South San Francisco, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 373 days.

(21) Appl. No.: 13/815,874

(22) Filed: Mar. 15, 2013

(65) Prior Publication Data

US 2014/0275181 A1    Sep. 18, 2014

(51) Int. Cl.
| | | |
|---|---|---|
| *C07D 401/04* | (2006.01) | |
| *C07D 498/08* | (2006.01) | |
| *C07D 213/74* | (2006.01) | |
| *C07D 403/04* | (2006.01) | |
| *C07D 491/107* | (2006.01) | |

(52) U.S. Cl.
CPC ......... *C07D 498/08* (2013.01); *C07D 213/74* (2013.01); *C07D 401/04* (2013.01); *C07D 403/04* (2013.01); *C07D 491/107* (2013.01)

(58) Field of Classification Search
CPC .................................................. C07D 401/04
See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Balani |
| 5,290,941 A | 3/1994 | Volante et al. |
| 5,403,816 A | 4/1995 | Takabe et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 11/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,593,472 B2 | 7/2003 | Hoffmann et al. |
| 6,608,076 B1 | 8/2003 | Greenwald et al. |
| 6,630,496 B1 | 10/2003 | Seehra et al. |
| 7,160,910 B2 | 1/2007 | Safo et al. |
| 7,411,083 B2 | 8/2008 | Gopalsamy et al. |
| 9,018,210 B2 | 4/2015 | Metcalf et al. |
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann et al. |
| 2009/0163512 A1 | 6/2009 | Chen et al. |
| 2009/0312315 A1 | 12/2009 | Yamaguchi et al. |
| 2010/0204235 A1 | 8/2010 | Lizos et al. |
| 2010/0311748 A1 | 12/2010 | Dakin et al. |
| 2012/0220569 A1 | 8/2012 | Ohashi et al. |
| 2013/0190316 A1 | 7/2013 | Metcalf et al. |
| 2013/0190375 A1 | 7/2013 | Dunkel et al. |
| 2015/0133430 A1 | 5/2015 | Xu et al. |
| 2015/0141465 A1 | 5/2015 | Yee et al. |

FOREIGN PATENT DOCUMENTS

| | | |
|---|---|---|
| CN | 101113148 | 1/2008 |
| CN | 102116772 | 7/2011 |
| DE | 22 38 734 | 2/1973 |
| DE | 22 38 628 | 3/1973 |
| DE | 28 53 765 | 6/1980 |

(Continued)

OTHER PUBLICATIONS

Ijeoma N. Nnamani, Gajanan S. Joshi, Richmond Danso-Danquah, Osheiza Abdulmalik, Toshio Asakura, Donald J. Abraham, and Martin K. Safo, Pyridyl Derivatives of Benzaldehyde as Potential Antisickling Agents, Chemistry & Biodiversity—vol. 5 (2008), 1762-1769.*

(Continued)

*Primary Examiner* — Sarah Pihonak
*Assistant Examiner* — Jason A Deck
(74) *Attorney, Agent, or Firm* — Jones Day

(57) ABSTRACT

Provide herein are compounds and pharmaceutical compositions suitable as modulators of hemoglobin, methods and intermediates for their preparation, and methods for their use in treating disorders mediated by hemoglobin and disorders that would benefit from tissue and/or cellular oxygenation.

3 Claims, No Drawings

(56) References Cited

FOREIGN PATENT DOCUMENTS

| | | |
|---|---|---|
| DE | 29 04 829 | 8/1980 |
| DE | 35 03 435 | 8/1985 |
| DE | 34 31 004 | 3/1986 |
| DE | 37 04 223 | 8/1987 |
| DE | 258226 | 7/1988 |
| DE | 276479 | 2/1990 |
| DE | 39 31 954 | 3/1990 |
| DE | 43 18 550 | 12/1994 |
| DE | 44 42 050 | 5/1996 |
| EP | 0 100 63 | 4/1980 |
| EP | 0054924 A2 * | 6/1982 |
| EP | 0 278 686 | 8/1988 |
| EP | 0 291 916 | 11/1988 |
| EP | 0 303 465 | 2/1989 |
| EP | 0 336 369 | 10/1989 |
| EP | 0 348 155 | 12/1989 |
| EP | 0 401 517 | 12/1990 |
| EP | 0 453 210 | 10/1991 |
| EP | 0 462 800 | 12/1991 |
| EP | 0 481 802 | 4/1992 |
| EP | 0 498 380 | 8/1992 |
| EP | 0 528 337 | 2/1993 |
| EP | 0 542 372 | 5/1993 |
| EP | 0 567 133 | 10/1993 |
| EP | 0 640 609 | 3/1995 |
| EP | 0 747 393 | 12/1996 |
| FR | 2217016 | 1/1900 |
| FR | 2909379 | 6/2008 |
| GB | 1 409 865 | 10/1975 |
| GB | 1 593 417 | 7/1981 |
| JP | 61-040236 | 2/1986 |
| JP | 06-041118 | 2/1994 |
| JP | 07-025882 | 1/1995 |
| JP | 2006-342115 | 12/2006 |
| JP | 2009-203230 | 9/2009 |
| WO | WO-91/19697 | 12/1991 |
| WO | WO-92/02503 | 2/1992 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO-97/44306 | 11/1997 |
| WO | WO-98/08818 | 3/1998 |
| WO | WO-98/21199 | 5/1998 |
| WO | WO-99/43672 | 9/1999 |
| WO | WO-99/47529 | 9/1999 |
| WO | WO-99/48490 | 9/1999 |
| WO | WO-99/59978 | 11/1999 |
| WO | WO-99/62908 | 12/1999 |
| WO | WO-00/35858 | 6/2000 |
| WO | WO-00/40564 | 7/2000 |
| WO | WO-00/71123 | 11/2000 |
| WO | WO-00/75145 | 12/2000 |
| WO | WO-01/00612 | 1/2001 |
| WO | WO-01/19823 | 3/2001 |
| WO | WO-01/23383 | 4/2001 |
| WO | WO-01/36375 | 5/2001 |
| WO | WO-01/57006 | 8/2001 |
| WO | WO-01/57044 | 8/2001 |
| WO | WO-01/62705 | 8/2001 |
| WO | WO-01/70663 | 9/2001 |
| WO | WO-02/00622 | 1/2002 |
| WO | WO-02/12235 | 2/2002 |
| WO | WO-02/24635 | 3/2002 |
| WO | WO-02/24679 | 3/2002 |
| WO | WO-02/051849 | 7/2002 |
| WO | WO-02/053547 | 7/2002 |
| WO | WO-03/051366 | 6/2003 |
| WO | WO-03/053368 | 7/2003 |
| WO | WO-03/101959 | 12/2003 |
| WO | WO-2004/018430 | 3/2004 |
| WO | WO-2004/024705 | 3/2004 |
| WO | WO-2004/050030 | 6/2004 |
| WO | WO-2004/056727 | 7/2004 |
| WO | WO-2004/058790 | 7/2004 |
| WO | WO 2004/087075 | 10/2004 |
| WO | WO-2005/074513 | 8/2005 |
| WO | WO-2005/077932 | 8/2005 |
| WO | WO-2005/087766 | 9/2005 |
| WO | WO-2006/011469 | 2/2006 |
| WO | WO-2006/088173 | 8/2006 |
| WO | WO-2006/103463 | 10/2006 |
| WO | WO-2006/106711 | 10/2006 |
| WO | WO-2006/116764 | 11/2006 |
| WO | WO-2007/003962 | 1/2007 |
| WO | WO-2007/009389 | 1/2007 |
| WO | WO-2007/017267 | 2/2007 |
| WO | WO-2007/047204 | 4/2007 |
| WO | WO-2007/049675 | 5/2007 |
| WO | WO-2007/117180 | 10/2007 |
| WO | WO-2008/013414 | 1/2008 |
| WO | WO-2008/016132 | 2/2008 |
| WO | WO-2008/041118 | 4/2008 |
| WO | WO-2008/051532 | 5/2008 |
| WO | WO-2008/060391 | 5/2008 |
| WO | WO-2008/081096 | 7/2008 |
| WO | WO-2008/101682 | 8/2008 |
| WO | WO-2008/116620 | 10/2008 |
| WO | WO-2009/001214 | 12/2008 |
| WO | WO-2009/050183 | 4/2009 |
| WO | WO-2009/125606 | 10/2009 |
| WO | WO-2009/130560 | 10/2009 |
| WO | WO-2009/136889 | 11/2009 |
| WO | WO-2009/146555 | 12/2009 |
| WO | WO-2010/031589 | 3/2010 |
| WO | WO-2010/056631 | 5/2010 |
| WO | WO-2010/129055 | 11/2010 |
| WO | WO-2011/033045 | 3/2011 |
| WO | WO-2011/136459 | 11/2011 |
| WO | WO-2012/138981 | 10/2012 |
| WO | WO-2012/141228 | 10/2012 |
| WO | WO-2013/102142 | 7/2013 |
| WO | WO-2013/102145 | 7/2013 |

OTHER PUBLICATIONS

Camille G. Wermuth, Molecular Variations Based on isosteric Replacements, The Practice of Medicinal chemistry, 1996, 203-232.*

George A. Patani and Edmond J. LaVoie, Bioisosterism: A Rational Approach in Drug Design, Chem. Rev. 1996, 96, 3147-3176.*

Beaumont et al., Design of ester prodrugs to enhance oral absorption of poorly permeable compounds: challenges to the discovery scientist. Curr. Drug Metab. 2003, 4:461-85.

Mantyla et al., Synthesis, in vitro evaluation and antileishmanial activity of water-soluble prodrugs of buparvaquone. J. Med. Chem. 2004, 47:188-195.

Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.

Rooseboom et al., Enzyme-catalyzed activation of anticancer prodrugs. Pharmacol. Rev. 2004, 56:53-102.

Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.

U.S. Appl. No. 13/815,776, filed Mar. 15, 2013, Qing Xu.
U.S. Appl. No. 13/815,770, filed Mar. 15, 2013, Brian W. Metcalf.
U.S. Appl. No. 13/815,735, filed Mar. 15, 2013, Qing Xu.
U.S. Appl. No. 14/207,289, filed Mar. 12, 2014, Zhe Li.
U.S. Appl. No. 13/815,872, filed Mar. 15, 2013, Brian W. Metcalf.
U.S. Appl. No. 13/815,810, filed Mar. 15, 2013, Brian W. Metcalf.
U.S. Appl. No. 14/010,455, filed Aug. 26, 2013, Jason R. Harris.
U.S. Appl. No. 14/776,713, filed Mar. 10, 2014, Harris et al.
U.S. Appl. No. 14/776,603, filed Mar. 10, 2014, Metcalf et al.
U.S. Appl. No. 14/776,717, filed Mar. 10, 2014, Li et al.

(56) References Cited

OTHER PUBLICATIONS

U.S. Appl. No. 14/776,711, filed Mar. 10, 2014, Sinha et al.
U.S. Appl. No. 14/776,715, filed Mar. 10, 2014, Li et al.
U.S. Appl. No. 14/776,726, filed Mar. 10, 2014, Xu et al.
U.S. Appl. No. 14/776,723, filed Mar. 14, 2014, Metcalf et al.
U.S. Appl. No. 14/216,346, filed Mar. 17, 2014, Li et al.
U.S. Appl. No. 14/662,145, filed Mar. 18, 2015, Metcalf et al.
U.S. Appl. No. 14/662,156, filed Mar. 18, 2015, Metcalf et al.
U.S. Appl. No. 14/791,017, filed Jul. 2, 2015, Xu et al.
U.S. Appl. No. 14/793,675, filed Jul. 7, 2015, Metcalf et al.
U.S. Appl. No. 14/809,151, filed Jul. 24, 2015, Dufu et al.
U.S. Appl. No. 14/836,869, filed Aug. 26, 2015, Xu et al.
Abdulmalik et al., Sickle cell disease: current therapeutic approaches, Expert Opinion Ther. Patents, 2005, vol. 15(11), pp. 1497-1506.
Abdulmalik et al., "Crystallographic analysis of human hemoglobin elucidates the structural basis of the potent and dual antisickling activity of pyridyl derivatives of vanillin." Acta Cryta. 2011, D67, pp. 920-928.
Abraham et al., Vanillin, a Potential Agent for the Treatment of Sickle Cell Anemia, Blood, Mar. 2005, vol. 77 (6), pp. 1334-1341.
Adhikary et al., "A new antisickling agent: In vitro studies of its effect on S/S erythrocytes and on hemoglobin S", Experientia. 1978, vol. 34, No. 6, pp. 804-806.
Bacsa et al., "Novel products from Baylis-Hillman reactions of salicylaldehydes", South African Journal of Chemistry (1998), 51(1), 47-54 CODEN: SAJCDG; ISSN: 0379-4350.
Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.
Ballet et al., Novel selective human melanocortin-3 receptor ligands: Use of the 4-amino-1,2,4,5-tetrahydro-2-benzazepin-3-one (Aba) scaffold, Bioorganic & Medicinal Chemistry Letters (2007), 17(9), 2492-2498 CODEN: BMCLES; ISSN: 0960-894X.
Baxter et al., "Reductive aminations of carbonyl compounds with borohydride and borane reducing agents", Organic Reactions (Hoboken, NJ, United States) (2002), 59, No pp. given bin/mrwhome/107610747/HOME.
Beddel, Sustituted benzaldehydes designed to increase the oxygen affinity of human haemoglobin and inhibit the sickling of sickle erythrocycles, Br. J. Pharmac., 82:397-407, 1984.
Berge et al., "Pharmaceutical Salts", Journal of Pharmaceutical Science, 1977, 66:1-19.
Bode et al.,"Novel synthesis and x-ray crystal structure of a coumarin derivative", South African Journal of Chemistry (1992), 45(1), 25-7 CODEN: SAJCDG; ISSN:0379-4350.
Bradbury et al., "New nonpeptide angiotensin II receptor antagonists", Journal of Medicinal Chemistry, vol. 36, Aug. 28, 1993 (Aug. 28, 1993), pp. 1245-1254.
Britton et al., "Structure-activity relationships of a series of benzothlophens-derived NPY Y1 antagonists: optimization of the C-2 side chain". Bioorganic & Medicinal Chemistry Letters (1999), 9(3), 475-480 CODEN:BMCLE8;ISSN: 0960-894X.
Brown et al., "1,2-Dihydroisoquinollnes. III, Dimerization", Tetrahedron (1966), 22(8), 2437-43 CODEN: TETRAB; ISSN;0040-4020.
Chemical Abstract Registry No. 1142191-55-6, indexed in the Registry File on STN CA Online May 4, 2009.
Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine (6-Amino PA-824).," J. Med. Chem., Aug. 2011, vol. 54(16), pp. 5639-5659.
Ciganek, "The catalyzed a-hydroxyalkylation and a-aminoalkylation of activated olefins (the Morita-Baylis-Hillman reaction", Organic Reactions (Hoboken, NJ, United States) (1997), 51, No pp given CODEN:ORHNBA URL:http://www3.Interscience.wiley.com/cgi-bin/mnwhome/107610747/HOME.

Cos et al., "Structure-Activity Relationship and Classification of Flavonoids as Inhibitors of Xanthine Oxidase and Superoxide Scavengers," J. Nat. Prod., (1998), 61:71-76.
Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (Abstract); RN:1427163-92-5 & CN 102 952 062 A, Mar. 6, 2013, 2 pages.
Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, vol. 26, No. 4, Jun. 1, 1991 (1991-86-81), pp. 455-468.
Ding et al., "Crystal structure of bis[μ2-2-(2-formylphenoxy)acetato-O,O]-bis[μ2-2-2-formylphynoxy)acetato-O,O]-octakis(n-butyl)tetratin(IV), Sn4O2(C9H7O4)4(C4H9)8", Zeitschrift fuer Kristallographie—New Crystal Structures (2011), 226(1), 31-32 CODEN:ZKNSFT; ISSN: 1433-7266.
Elwahy, "Synthesis of new benzo-substituted macrocyclic containing quinoxaline subunits" Tetrahedron (2000), 56(6), 897-907 CODEN:TETRAB; ISSN:0040-4020.
EP Search Report for Application No. 12862096.0 dated May 28, 2015.
Epsztajn et al., "Application of organolithium", Tetrahedron, Elsevier Science Publishers, Amsterdam, NL, vol. 47, No. 9, Jan. 1, 1991 (Jan. 1, 1991), pp. 1697-1706.
Gadaginamath et al., "Synthesis and antibacterial activity of novel 1-butyl-2-phenoxyl2-phenylthlol2-aminomethyl-5-methoxyindole derivatives", Polish Journal of Chemistry (1997), 71(7), 923-928 CODEN: PJCHDQ; ISSN:0137-5083.
Gao et al, "A novel one-pot three-step synthesis of 2-(1-benzofuran-2-yl)quinoline-3-carboxylic acid derivatives", Journal of the Brazilian Chemical Society (2010), 21(5). 806-812 CODEN:JOCSET; ISSN: 0103-5053.
Ghate et al., "Synthesis of vanillin ethers from 4-(bromomethyl) counmarins as anti-inflammatory agents," European Journal of Medicinal Chemistry (2003), 38(3), 297-302 CODEN: EJMCA5; ISSN: 0223-5234.
Gibson et al., "Novel small molecule bradykinin B2 receptor antagonists", Journal of Medicinal Chemistry, vol. 52, Feb. 26, 2009 (Feb. 26, 2009), pp. 4370-4379.
Grashey, "The nitro group as a 1,3-dipole in cycloadditions" Angewandfe Chemie (1962), 74, 155 CODEN: ANCEAD; ISSN: 0044-8249.
Gunter et al., "Structural control of co-receptor binding in porphyrin-bipyridinium supramolecular assemblies", Journal of the Chemical Society, Perkin Transactions 1: Organic and Bio-Organic Chemistry (1998), (12), 1945-1958 CODEN: JCPRB4; ISSN: 0300-922X.
Hanmantgad et al., "Synthesis and pharmacological properties of some r-(2-benzo[b]furanyl)coumarins" Indian Journal of Chemistry, Section B: Organic Chemistry Including Medicinal Chemistry (1986), 25B(7), 779-81 CODEN: IJSBDB; ISSN: 0376-4699.
He et al., "Prodrugs of Phosphonates, Phosphinates, and Phosphates", Prodrugs: Challenges and rewards Part 2, edited by Stella et al., 2007, pp. 223-264.
Heimbach et al., "Enzyme-mediated precipitation of patent drugs from their phosphate prodrugs", International Journal of Pharmaceutics, 261, p. 81-92, 2002.
Heimbach et al., "Prodrugs: Challenges and Rewards Part I," New York, NY, Singer:AAPS Press, (2007), 5(Chapter 2.2.1):157-215 Overcoming Poor Aqueous Solubility of Drigs for Oral Delivery.
Heimgartner et al., "Stereoselective synthesis of swainsonines from pyridines", Tetrahedron, Elsevier Science Publishers, Amsterdam, NL, vol. 61, No. 3, Jan. 17, 2004 (2085-81-17), pp. 643-655.
Hong et al., "Potential Anticancer Agents VI: 5-Substituted Pyrimidine-6-Carboxaldehydes", Journal of Pharmaceutical Sciences, American Pharmaceutical Association, Washington, US, vol. 59, No. 11, Nov. 1, 1970 (Nov. 1, 1970), pp. 1637-1645.

(56) References Cited

OTHER PUBLICATIONS

Ito et al., A medium-term rat liver bioassay for rapid in vivo detection of carcinogenic potential of chemicals,01D Cancer Science, 2005, 94, pp. 3-8.
Jarvest et al., "Discovery and optimisation of potent, selective, ethanolamine Inhibitors of bacterial phynylalanyl tRNA synthetase", Bioorganic & Medicinal Chemistry Letter (2005), 15(9), 2305-2309 CODEN: BMCLES; ISSN: 0960-894X.
Karche et al., "Electronic Effects in Migratory Groups [1,4]- versus [1,2]- Rearrangement in Rhodium Carbenoid Generated Bicyclic Oxonlum Ylides", Journal of Organic Chemistry (2001), 66(19), 6323-6332 CODEN: JOCEAH; ISSN: 0022-3263.
Katritzky et al., "Synthesis of 3-hydroxymethyl-2-3-dihydrobenzofurans and 3-hydroxymethylbenzofurans", ARKIVOC (Gainesville, FL, United States) (2003), (6), 49-61 CODEN: AGFUAR URL: http://www.arkat-usa.org/ark/journal/2003/Vargoglis/AV-622A/6ss.pdf.
Kaye et al., "DABCO-catalyzed reactions of salicylaidehydes with acrylate derivatives", Synthetic Communications (1996), 26(11), 2085-97 CODEN: SYNCAV; ISSN: 0039-7911.
Kaye et al., "Does the DABCO-catalyzed reaction of 2-hydroxybenzaldehydes with methyl acrylate follow a Baylis-Hillman pathway?", Organic & Biomolecular Chemistry (2003), 1(7), 1133-1138 CODEN: OBCRAK; ISSN: 1477-0520.
Kessar et al., "Synthesis of Isoindolobenzazepines via photocyclization of N-(2-formylphenelhyl)phthalimide derivatives", Indian Journal of Chemistry, Section B: Organic Chemistry Including Medicinal Chemistry (1991), 30B(11), 999-1005 CODEN: JSBDB; ISSN:3076-4699.
Kessar et al., Tetrahedron Letters (1987), 28(44), 5323-6 CODEN: TELEAY; ISSN: 0040-4039.
Kise et al., "Electroreductive Intramolecular Coupling of Phthalimides with Aromatic Aldehydes: Application to the Synthesis of Lennoxamine". Journal of Organic Chemistry (2011), 76(23), 9658-9880 CODEN:JOCEAH; ISSN: 0022-3263.
Krow,"The Baeyer-Villiger oxidation of ketones and aidehydes", Organic Reactions (Hoboken, NJ, United States) (1993), 43, No pp. given CODEN: ORHNBA URL: http://www3.interscience.wiley.com/cgi- bin/mrwhome/107610747/HOME.
Lakkannavar et al., "4-[2'-benzylideneanllino aryloxymethyl] coumarins E and Z isomers". Indian Journal of Heterocycilc Chemistry (1995), 4(4), 303-4 CODEN: IJCHEI; ISSN: 0971-1627.
Lin et al., "Potential Antitumor Agents.8. Derivatives of 3- and 5-Benzyloxy-2-formylpyridine Thiosemicarbazone", Journal of Medicinal Chemistry, American Chemical Society, US, vol. 15, No. 6, Jan. 1, 1972 (1972-01-81), pp. 615-618.
Liu et al., "Synthesis of Double-Armed Benzo-15-crown-5 and Their Complexation Thermodynamics with Akal Cations", Journal of Inclusion Phenomena and Macrocyclic Chemistry (2005), 52(3-4), 229-235 CODEN: JIPCF5; ISSN: 1388-3127.
Mahoney et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters (2009), 50(33), 4706-4709 CODEN: TELEAY; ISSN: 0040-4039.
Majhi et al., "An efficient synthesis of novel dibenzo-fused nine-membered oxacycles using a sequential Baylis-Hillman reaction and radical cyclization", Synthesis (2008), (1), 94-100 CODEN: SYNTBF; ISSN: 0039-7881.
Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, Il Farmaco, vol. 51, No. 8, 9, Jan. 1, 1996 (Jan. 1, 1996), pp. 579-587.
Marchetti et al., "Synthesis and biological evaluation of 5-substituted O4-alkylpyrimidines as CDK2 inhibitors," Org. Biomol. Chem, 2010, vol. 8, pp. 2397-2407.
McKay et al., 7,11,15,28- Tetrakis[(2-formylphenoxy)methyl]-1,21,23,25-tetramethylresorcin[4]arene cavitand ethyl acetate ciathrate at 173 K, Acta Crystallographica, Section E: Structure Reports Online (2009), E65(4), 692-693 CODEN: ACSEBH; ISSN: 1600-5368 URL: http://journals.lucr.org/e/issues/2009/04/00fl2233/fl2233.pdf.
McKay et al., "Microwave-assisted synthesis of a new series of resorcin[4]arena cavitand-capped porphyrin capsules", Organic & Biomolecular Chemistry (2009), 7(19), 3958-3968 CODEN: OBCRAK; ISSN: 1477-0520.
Merlino et al., "Development of second generation amidinohydrazones, thio- and semicarbazones as Trypanosoma cruzi-inhibitors bearing benzofuroxan and benzimidazole 1,3-dioxide core scaffolds" , MedChemComm (2010), 1(3), 216-228 CODEN: MCCEAY; ISSN: 2040-2503.
Mesguiche et al.,"4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.
Mitra et al., "Synthesis and biological evaluation of dibenz[b,f][1,5]oxazocine derivatives for agonist activity at x-oploid receptor", European Journal of Medicinal Chemistry (2011), 46(5), 1713-1720 CODEN: EJMCA5; ISSN: 0223-5234.
Mulwad et al., "Synthesis and anitmicrobial activity of [6'-methyl-4'-methoxy-2-oxo-2H-[1]-benzopyran)-2",4" dihydro-[1",2", 4"]-3'-one and 3'phenylthiazolidin-4'-one-phenoxymethyl derivatives of dipyranoquinoline", Pharmaceutical Chemistry Journal Ahead of Print CODEN: PCJOAU; ISSN: 0091-150, 2011.
Neelima et al., "A novel annelation reaction: synthesis of 6H-[1]benzopyrano[4,4-b]quinoiones" Chemistry & Industry (London, United Kingdom) (1986), (4), 141-2 CODEN: CHINAG; ISSN: 0009-3068.
Nnamani et al., "Pyridyl derivatives of benzaldehyde as potential antisickling agents," Chem. Biodivers., (2008), 5(9):1762-1769.
Nogrady, Medicinal Chemistry A Biochemical Approach, Oxford University Press, New York, pp. 388-392 (1985).
Nonoyama et al.,"Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron 1999, 533-543 CODEN: PLYHDE; ISSN: 0277-5387.
Nyerges et al, "Synthesis of Indazole N-oxides via the 1.7-electrocyclization of azomethine ylides", Tetrahedron Letters (2001), 42(30), 5081-5083 CODEN: TELEAY; ISSN:0040-4039.
Nyerges et al, "Synthesis of Indazole N-oxides via the 1.7-electrocyclization of azomethine ylides", Tetrahedron Letters (2004), 60(44), 9937-9944 CODEN: TETRAB; ISSN:0040-4020.
OECD SIDS "SIDS Initial Assessment Report for 13th SIAM," Nov. 2001, pp. 1-95.
O'Reilly, "Metal-phenoxyalkanoic acid interactions, XXV. The crystal structures of (2-formyl-6-methoxyphenoxy)acetic acid and its zinc(II)complex and the lithium, zinc(II) and cadmium(II) complexes of (2-chlorophenoxy)acetic acid", Australian Journal of Chemistry (1987), 40(7)m 1146-59 CODEN; AJCHAS; ISSN:0004-9425.
PCT International Search Report and Written Opinion dated Aug. 19, 2014 for PCT Application No. PCT/US2014/022736.
PCT International Search Report and Written Opinion dated Jul. 22, 2014 for PCT Application No. PCT/US2014/022846.
PCT International Search Report and Written Opinion dated Jul. 31, 2014 for PCT Application No. PCT/US2014/022789.
PCT International Search Report and Written Opinion dated Aug. 27, 2014 for PCT Application No. PCT/US2014/022742.
Perez et al., "Preparation of new 1,2-disubstituted ferrocenyl ammonium salt", Polyhedron (2009), 28(14), 3115-3119 CODEN: PLYHE; ISSN:0277-5387.
Perkins et al., "Manganese(II), Iron(II), cobalt(II), and cooper(II)complexes of an extended inherently chiral tris-bipyricyl cage", Proceedings of the National Academy of Sciences of the United States of America (2006), 103(3), 532-537 CODEN: PNASA6; ISSN: 0027-8424.
PUBCHEM CID 54009805 Create Date: Dec. 4, 2011 p. 1.
PUBCHEM CID 54883281 Create Date: Aug. 19, 2012 p. 1.
Ruchirawat et al., "A novel synthesis of aporhoeadanes", Tetrahedron Letters (1984), 25(32), 3485-8 CODEN: TELEAY; ISSN: 0040-4039.

(56) References Cited

OTHER PUBLICATIONS

Sahakitpichan et al., "A practical and highly efficient synthesis of lennoxamine and related isoindoloenzazepines" Tetrahedron (2004), 60(19), 4169-4172 CODEN: TETRAB; ISSN: 0040-4020.

Sahm et al., "Synthesis of 2-arylbenzofurans" Justus Liebigs Annalen der Chemie (1974), (4), 523-38 CODEN: JLACBF; ISSN: 0075-4617. (Abstract).

Sainsbury et al., "1,2-Dihydroisoquinolines, IV. Acylation" Tetrahedron (1966), 22(8), 2445-52 CODEN: TETRAB; ISSN: 0040-4020.

Sarodnick et al., "Quinoxalines XV, Convenient Synthesis and Structural Study of Pyrazolo[1,5-a]quinoxalines", Journal of Organic Chemistry (2009), 74(3), 1282-1287 CODEN: JOCEAH; ISSN: 0022-3263.

Siddiqui et al., "The Presence of Substitutents on the Aryl Moiety of the Aryl Phosphoramidate Derivative of d4T Enhances Anti-HIV Efficasy in Cell Culture-Activity Relationship," J. Med. Chem., (1999), 42:393-399.

Silva et al., "Advances in prodrug design," Mini Rev. Med. Chem., (2005), 5(10):893-914.

Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.

Srivastava et al., "Synthesis adn biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.

Starke et al., "Quinoxalines, Part 13: Syntesis and mass spectrometric study of aryloxymethylquinoxalines and benzo[b]furylquinoxalines" Tetrahedron (2004), 60(29), 6063-6078 CODEN: TETRAB; ISSN:0040-4020.

Swann et al., "Rates of reductive elimination of substituted nitrophenois from the (indol-3-yl)methyl position of indolequinones", Journal of the Chemical Society, Perkin Transactions 2 (2001), (8), 1340-1345.

Testa et al., Hydrolysis in Drug and Prodrug Metabolism, Jun. 2003, Wiley—VCH, Zurich, 419-534.

Tome et al., "Product class 13: 1,2,3-triazoles", Science of Synthesis (2004), 13, 415-601 CODEN: SSCYJ9.

vanRompaey et al., "A versatile synthesis of 2-substituted 4-amino-1,2,4,5-tetrahydro-2-benzazepine-3-ones", Tetrahedron (2003), 59(24), 4421-4432 CODEN: TETRAB; ISSN:0040-4020.

vanRompaey et al., "Synthesis and evaluation of the 3B2-turn properties of 4-amino-1,2,4,5-tetrahydro-2-benzazepin-3-ones and of their spirocyclic derivative", European Journal of Organic Chemistry (2006), (13), 2899-2911 CODEN: EJOCFK; ISSN: 1434-193X.

Vicente et al., "Carbopalladation of Maleate and Fumarate Esters and 1,1-Dimethylallene with Ortho-Substituted Aryl Palladium Complexes" Organometallics (2010), 29(2), 409-416.

Wang et al., "Studies of Benzothiophane Template as Potent Factor IXa (FIXa) Inhibitors in Thrombosis", Journal of Medicinal Chemistry (2010), 53, 1465-1472.

Warshawsky et al., "The synthesis of aminobenzazespinones as anti-phenylalanine dipeptide mimics and their use in NEP inhibition", Bioorganic & Medicinal Chemistry Letter (1996), 6(8), 957-962 CODEN: BMCLE8; ISSN: 0960-894X.

Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.

Yan et al., "Synthesis, crystal structure and antibacterial activity of dibutylitin carboxylate", Huaxue Tongbao (2007), 70(4), 313-316 CODEN: HHTPAU; ISSN: 0441-3776. (Abstract).

Yan et al., "Synthesis, crystal structure and antibacterial activity of di-n-butyltin di-2(2-formylphenoxy)acetic ester", Yingyong Huaxue (2007), 24(6), 660-664. (Abstract).

Yoon et al., The Chirality conversion reagent for amino acids based on salicyl aldehyde. Bull. Korean Chem. Soc., (2012), 33:1715-18.

Zhang et al., "DFT study on RuII-catalyzed cyclization of terminal alkynals to cycloalkenes", International Journal of Quantum Chemistry (2009), 109(4), 679-687 CODEN: IJQCB2; ISSN:0020-7608.

Zhu et al., "Isoquinoline-pyridine-based protein kinase B/Akt antagonists: SAR and in vivo antitumor activity", Bioorganic & Medicinal Chemistry Letters, Pergamon, Amsterdam, NL, vol. 16, No. 12, Jun. 15, 2006 (Jun. 15, 2006), pp. 3150-3155.

Zwaagstra et al., "Synthesis and Structure-Activity Relationships of Carboxylated Chalcones: A Novel Series of Cys-LT1 (LTD4) Recaptor Antagonists", Journal of Medicinal Chemistry (1997), 40(7), 1075-1089 CODEN: JMCMAR; ISSN: 0022-2623.

Rolan et al., "The pharmacokinetics, tolerability and pharmacodynamics of tucaresol (589C80; 4[2-formyl-3-hydroxyphenoxymethyl] benzoic acid), a potential anti-sickling agent, following oral administration to healthy subjects", Br. J. Clin. Pharmacol., 35(4):419-425 (1993).

\* cited by examiner

COMPOUNDS AND USES THEREOF FOR THE MODULATION OF HEMOGLOBIN

FIELD OF THE INVENTION

This invention provides compounds and pharmaceutical compositions suitable as allosteric modulators of hemoglobin, methods and intermediates for their preparation, and methods for their use in treating disorders mediated by hemoglobin and disorders that would benefit from tissue and/or cellular oxygenation.

STATE OF THE ART

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin (Hb).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, allowing HbS to become susceptible to polymerization to give the HbS containing red blood cells their characteristic sickle shape. The sickled cells are also more rigid than normal red blood cells, and their lack of flexibility can lead to blockage of blood vessels. U.S. Pat. No. 7,160,910 discloses compounds that are allosteric modulators of hemoglobin. However, a need exists for additional therapeutics that can treat disorders that are mediated by Hb or by abnormal Hb such as HbS.

SUMMARY OF THE INVENTION

This invention relates generally to compounds and pharmaceutical compositions suitable as allosteric modulators of hemoglobin. In some aspects, this invention relates to methods for treating disorders mediated by hemoglobin and disorders that would benefit from tissue and/or cellular oxygenation.

In certain aspects of the invention, a compound of formula (I) is provided:

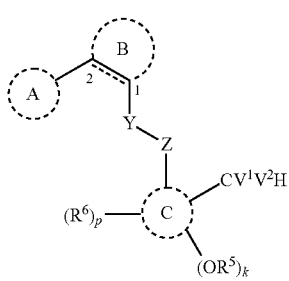

or a tautomer thereof, or a pharmaceutically acceptable salt of each thereof, wherein ring A is an optionally substituted 4-10 membered cycloalkyl or 4-10 membered heterocycle containing up to 5 ring heteroatoms, wherein the heteroatom is selected from the group consisting of O, N, S, and oxidized forms of N and S;

ring B is a $C_6$-$C_{10}$ aryl or 5-10 membered heteroaryl having 1-3 nitrogen atoms, preferably 1-2 nitrogen atoms and more preferably 1 nitrogen atom, or oxidized versions thereof, wherein the aryl or heteroaryl is optionally substituted;

⁓ is a single or a double bond;

each Y and Z is independently $CR^{10}R^{11}$, O, S, SO, $SO_2$, or $NR^{12}$; each $R^{10}$ and $R^{11}$ independently is hydrogen or $C_1$-$C_3$ alkyl optionally substituted with halo, OH, or $C_1$-$C_6$ alkoxy, or $CR^{10}R^{11}$ is C=O; $R^{12}$ is hydrogen or $C_1$-$C_6$ alkyl; provided that if one of Y and Z is O, S, SO, $SO_2$, then the other is not CO, and provided that Y and Z are both not heteroatoms or oxidized forms thereof;

ring C is $C_6$-$C_{10}$ aryl;

$V^1$ and $V^2$ independently are $C_1$-$C_6$ alkoxy; or $V^1$ and $V^2$ together with the carbon atom they are attached to form a ring of formula:

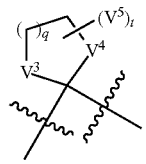

wherein each $V^3$ and $V^4$ are independently O, S, or NH, provided that when one of $V^3$ and $V^4$ is S, the other is NH, and provided that $V^3$ and $V^4$ are both not NH; q is 1 or 2; each $V_5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;

$R^5$ is hydrogen, $C_1$-$C_6$ alkyl or a prodrug moiety R, wherein the $C_1$-$C_6$ alkyl is optionally substituted with 1-5 halo;

$R^6$ is halo, $C_1$-$C_6$ alkyl, $C_1$-$C_6$ alkoxy, $C_1$-$C_6$ alkylthio, $C_1$-$C_6$S(O)—, $C_1$-$C_6$S(O)$_2$—, wherein the $C_1$-$C_6$ alkyl is optionally substituted with 1-5 halo; or $R^6$ is 4-10 membered cycloalkyl or heterocycle substituted with an R'R'N— moiety wherein each R' is independently $C_1$-$C_6$ alkyl or hydrogen;

$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;

$R^{83}$ is hydrogen or optionally substituted $C_1$-$C_6$ alkyl;

$R^{84}$ is optionally substituted $C_1$-$C_6$ alkyl;

k is 0 or 1; and p is 0, 1, 2 or 3.

In further aspects of the invention, a composition is provided comprising any of the compounds described herein, and at least a pharmaceutically acceptable excipient.

In still further aspects of the invention, a method is provided for increasing oxygen affinity of hemoglobin S in a subject, the method comprising administering to a subject in need thereof a therapeutically effective amount of any of the compounds or compositions described herein.

In further aspects of the invention, a method is provided for treating oxygen deficiency associated with sickle cell anemia, the method comprising administering to a subject in need thereof a therapeutically effective amount of any of the compounds or compositions described herein.

DETAILED DESCRIPTION OF THE INVENTION

Definitions

It must be noted that as used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

As used herein, $C_m$-$C_n$, such as $C_1$-$C_{12}$, $C_1$-$C_8$, or $C_1$-$C_6$ when used before a group refers to that group containing m to n carbon atoms.

The term "alkoxy" refers to —O-alkyl. The term alkylthio is —S-alkyl.

The term "alkyl" refers to monovalent saturated aliphatic hydrocarbyl groups having from 1 to 30 carbon atoms (i.e., $C_1$-$C_{30}$ alkyl) or 1 to 22 carbon atoms (i.e., $C_1$-$C_{22}$ alkyl), 1 to 8 carbon atoms (i.e., $C_1$-$C_8$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3$—$CH_2$)CH—), t-butyl (($CH_3$)$_3$C—), n-pentyl ($CH_3CH_2CH_2CH_2CH_2$—), and neopentyl ($CH_3$)$_3$CCH$_2$—).

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom. For example, and without limitation, the following is an aryl group:

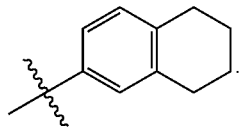 [SMILES: *c1ccc2c(c1)CCCC2]

The term "—$CO_2H$ ester" refers to an ester formed between the —$CO_2H$ group and an alcohol, preferably an aliphatic alcohol. A preferred example included —$CO_2R^E$, wherein $R^E$ is alkyl or aryl group optionally substituted with an amino group.

The term "chiral moiety" refers to a moiety that is chiral. Such a moiety can possess one or more asymmetric centers. Preferably, the chiral moiety is enantiomerically enriched, and more preferably a single enantiomer. Non limiting examples of chiral moieties include chiral carboxylic acids, chiral amines, chiral amino acids, such as the naturally occurring amino acids, chiral alcohols including chiral steroids, and the likes.

The term "cycloalkyl" refers to a monovalent, preferably saturated, hydrocarbyl mono-, bi-, or tricyclic ring having 3-12 ring carbon atoms. While cycloalkyl, refers preferably to saturated hydrocarbyl rings, as used herein, it also includes rings containing 1-2 carbon-carbon double bonds. Nonlimiting examples of cycloalkyl include cyclopropyl, cyclobutyl, cyclopentyl, cyclohexyl, cycloheptyl, adamentyl, and the like. The condensed rings may or may not be non-aromatic hydrocarbyl rings provided that the point of attachment is at a cycloalkyl carbon atom. For example, and without limitation, the following is a cycloalkyl group:

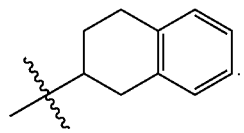

The term "halo" refers to F, Cl, Br, and/or I.

The term "heteroaryl" refers to a monovalent, aromatic mono-, bi-, or tricyclic ring having 2-16 ring carbon atoms and 1-8 ring heteroatoms selected preferably from N, O, S, and P and oxidized forms of N, S, and P, provided that the ring contains at least 5 ring atoms. Nonlimiting examples of heteroaryl include furan, imidazole, oxadiazole, oxazole, pyridine, quinoline, and the like. The condensed rings may or may not be a heteroatom containing aromatic ring provided that the point of attachment is a heteroaryl atom. For example, and without limitation, the following is a heteroaryl group:

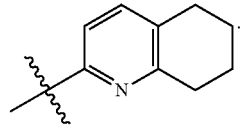

The term "heterocyclyl" or heterocycle refers to a non-aromatic, mono-, bi-, or tricyclic ring containing 2-12 ring carbon atoms and 1-8 ring heteroatoms selected preferably from N, O, S, and P and oxidized forms of N, S, and P, provided that the ring contains at least 3 ring atoms. While heterocyclyl preferably refers to saturated ring systems, it also includes ring systems containing 1-3 double bonds, provided that the ring is non-aromatic. Nonlimiting examples of heterocyclyl include, azalactones, oxazoline, piperidinyl, piperazinyl, pyrrolidinyl, tetrahydrofuranyl, and tetrahydropyranyl. The condensed rings may or may not contain a non-aromatic heteroatom containing ring provided that the point of attachment is a heterocyclyl group. For example, and without limitation, the following is a heterocyclyl group:

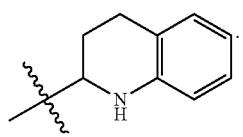 [SMILES: *C1CCc2ccccc2C1]

The term "hydrolyzing" refers to breaking an $R^H$—O—CO—, $R^H$—O—CS—, or an $R^H$—O—$SO_2$-moiety to an $R^H$—OH, preferably by adding water across the broken bond. A hydrolyzing is performed using various methods well known to the skilled artisan, non limiting examples of which include acidic and basic hydrolysis.

The term "oxo" refers to a C=O group, and to a substitution of 2 geminal hydrogen atoms with a C=O group.

The term "optionally substituted" refers to a substituted or unsubstituted group. The group may be substituted with one or more substituents; such as e.g., 1, 2, 3, 4 or 5 substituents. Preferably, the substituents are selected from the group consisting of oxo, halo, —CN, $NO_2$, —$N_2$+, —$CO_2R^{100}$, —$OR^{100}$, —$SR^{100}$, $SOR^{100}$, —$SO_2R^{100}$, —$CONR^{101}R^{102}$, —$SO_2NR^{101}R^{102}$, $C_1$-$C_6$ alkyl, $C_1$-$C_6$ alkoxy, —$CR^{100}$=C($R^{100}$)$_2$, —$CCR^{100}$, $C_3$-$C_{10}$ cycloalkyl, $C_3$-$C_{10}$ heterocyclyl, $C_6$-$C_{12}$ aryl and $C_2$-$C_{12}$ heteroaryl, wherein each $R^{100}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; wherein each alkyl, cycloalkyl, heterocyclyl, aryl, or heteroaryl is optionally substituted with 1-3 halo, 1-3 $C_1$-$C_6$ alkyl, 1-3 $C_1$-$C_6$ haloalkyl or 1-3 $C_1$-$C_6$ alkoxy groups. Preferably, the substituents are selected from the group consisting of chloro, fluoro, —$OCH_3$, methyl, ethyl, isopropyl, cyclopropyl, vinyl, ethynyl, —$CO_2H$, —$CO_2CH_3$, —$OCF_3$, —$CF_3$ and —$OCHF_2$.

$R^{101}$ and $R^{102}$ independently is hydrogen; $C_1$-$C_8$ alkyl, optionally substituted with —$CO_2H$ or an ester thereof, $C_1$-$C_6$ alkoxy, oxo, —$CR^{103}$=C($R^{103}$)$_2$, —CCR, $C_3$-$C_{10}$ cycloalkyl, $C_3$-$C_{10}$ heterocyclyl, $C_6$-$C_{12}$ aryl, or $C_2$-$C_{12}$ heteroaryl, wherein each $R^{103}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; wherein each cycloalkyl, heterocyclyl, aryl, or heteroaryl is optionally substituted with 1-3 alkyl groups or 1-3 halo groups, or $R^{101}$ and $R^{102}$ together with the nitrogen atom they are attached to form a 5-7 membered heterocycle.

The term "pharmaceutically acceptable" refers to safe and non-toxic for in vivo, preferably, human administration.

The term "pharmaceutically acceptable salt" refers to a salt that is pharmaceutically acceptable.

The term "salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisalfate, mono-, di-, and tribasic phosphate, mesylate, tosylate, and the likes.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease). The terms further include causing the clinical symptoms not to develop, for example in a subject at risk of suffering from such a disease or disorder, thereby substantially averting onset of the disease or disorder.

The term "effective amount" refers to an amount that is effective for the treatment of a condition or disorder by an intranasal administration of a compound or composition described herein. In some embodiments, an effective amount of any of the compositions or dosage forms described herein is the amount used to treat a disorder mediated by hemoglobin or a disorder that would benefit from tissue and/or cellular oxygenation of any of the compositions or dosage forms described herein to a subject in need thereof.

The term "carrier" as used herein, refers to relatively nontoxic chemical compounds or agents that facilitate the incorporation of a compound into cells, e.g., red blood cells, or tissues.

As used herein, a "prodrug" is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity. For example, see the reference Nogrady, 1985, Medicinal Chemistry A Biochemical Approach, Oxford University Press, New York, pages 388-392. Prodrugs can also be prepared using compounds that are not drugs.

Compounds

In certain aspects of the invention, a compound of formula (I) is provided:

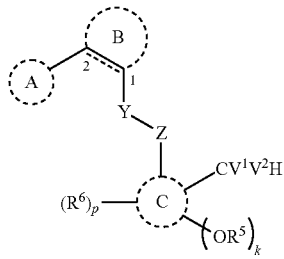

or a tautomer thereof, or a pharmaceutically acceptable salt of each thereof, wherein
ring A is an optionally substituted 4-10 membered cycloalkyl or 4-10 membered heterocycle containing up to 5 ring heteroatoms, wherein the heteroatom is selected from the group consisting of O, N, S, and oxidized forms of N and S;
ring B is a $C_6$-$C_{10}$ aryl or 5-10 membered heteroaryl having 1-3 nitrogen atoms, preferably 1-2 nitrogen atoms and more preferably 1 nitrogen atom, or oxidized versions thereof, wherein the aryl or heteroaryl is optionally substituted;

⫶⫶⫶ is a single or a double bond;
each Y and Z is independently $CR^{10}R^{11}$, O, S, SO, $SO_2$, or $NR^{12}$; each $R^{10}$ and $R^{11}$ independently is hydrogen or $C_1$-$C_3$ alkyl optionally substituted with halo, OH, or $C_1$-$C_6$ alkoxy, or $CR^{10}R^{11}$ is C=O; $R^{12}$ is hydrogen or $C_1$-$C_6$ alkyl; provided that if one of Y and Z is O, S, SO, $SO_2$, then the other is not CO, and provided that Y and Z are both not heteroatoms or oxidized forms thereof;
ring C is $C_6$-$C_{10}$ aryl;
$V^1$ and $V^2$ independently are $C_1$-$C_6$ alkoxy; or $V^1$ and $V^2$ together with the carbon atom they are attached to form a ring of formula:

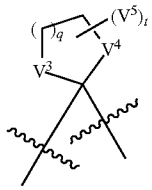

wherein each $V^3$ and $V^4$ are independently O, S, or NH, provided that when one of $V^3$ and $V^4$ is 5, the other is NH, and provided that $V^3$ and $V^4$ are both not NH; q is 1 or 2; each $V_5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, $NOR^{80}$, or $NNR^{81}R^{82}$;
$R^5$ is hydrogen, $C_1$-$C_6$ alkyl or a prodrug moiety R, wherein the $C_1$-$C_6$ alkyl is optionally substituted with 1-5 halo;
$R^6$ is halo, $C_1$-$C_6$ alkyl, $C_1$-$C_6$ alkoxy, $C_1$-$C_6$ alkylthio, $C_1$-$C_6$S(O)—, $C_1$-$C_6$S(O)$_2$—, wherein the $C_1$-$C_6$ alkyl is optionally substituted with 1-5 halo; or
$R^6$ is 4-10 membered cycloalkyl or heterocycle substituted with an R'R'N-moiety wherein each R' is independently $C_1$-$C_6$ alkyl or hydrogen;
$R^{80}$ is optionally substituted $C_1$-$C_6$ alkyl;

$R^{81}$ and $R^{82}$ independently are selected from the group consisting of hydrogen, optionally substituted $C_1$-$C_6$ alkyl, $COR^{83}$, or $CO_2R^{84}$;
$R^{83}$ is hydrogen or optionally substituted $C_1$-$C_6$ alkyl;
$R^{84}$ is optionally substituted $C_1$-$C_6$ alkyl;
k is 0 or 1; and
p is 0, 1, 2 or 3.

In certain embodiments, t is 0. In certain embodiments, t is 1. In certain embodiments, t is 2. In certain embodiments, t is 3.

Preferably, in certain embodiments, Y and Z are both not a heteroatom or a heteroatom containing moiety. Preferably, one of Y and Z is a methylene or substituted methylene and the other is a heteroatom or a heteroatom containing moiety. More preferably, Y is an alkylene, and Z is a heteroatom or a heteroatom containing moiety, which, yet more preferably is oxygen.

Preferably, $V^1$ and $V^2$ together with the carbon atom they are attached to form a ring of formula:

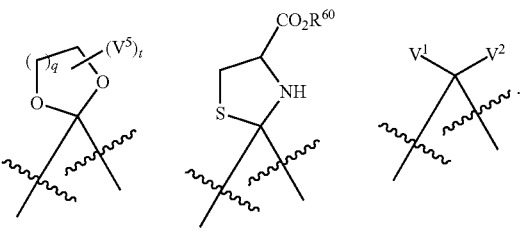

In some embodiments, $V^1$ and $V^2$ independently are $C_1$-$C_6$ alkoxy; or $V^1$ and $V^2$ together with the carbon atom they are attached to form a ring of formula:

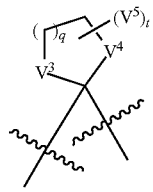

wherein each $V^3$ and $V^4$ are independently O, S, or NH, provided that when one or $V^3$ and $V^4$ is S the other is NH, and provided that $V^3$ and $V^4$ are both not NH; q is 1 or 2; each $V_5$ is independently $C_1$-$C_6$ alkyl or $CO_2R^{60}$, where each $R^{60}$ independently is $C_1$-$C_6$ alkyl or hydrogen; t is 0, 1, 2, or 4; or $CV^1V^2$ is C=V, wherein V is O, and wherein the remaining variables are defined herein.

In certain aspects of the invention, the compound of Formula (I) is of Formula (II):

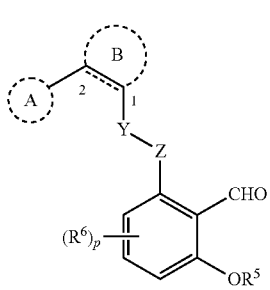

wherein the remaining variables are defined herein.

In certain aspects of the invention, the compound of Formula (I) is of Formula (IIA):

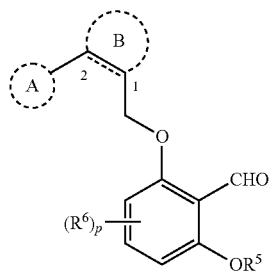
(II)

wherein
the variables are defined herein.

In some embodiments, ring A is optionally substituted with 1-3: halo, $C_1$-$C_6$ alkyl, $COR^{15}$ and/or $COOR^{15}$; wherein $R^{15}$ is optionally substituted $C_1$-$C_6$ alkyl, optionally substituted $C_6$-$C_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S.

In some embodiments, ring B is optionally substituted with 1-3: halo, $C_1$-$C_6$ alkyl $COR^{15}$ and/or $COOR^{15}$; wherein $R^{15}$ is optionally substituted $C_1$-$C_6$ alkyl, optionally substituted $C_6$-$C_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S.

In some embodiments, the compound is selected from the group consisting of

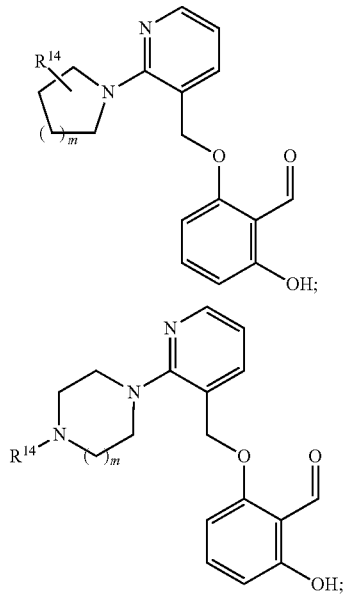

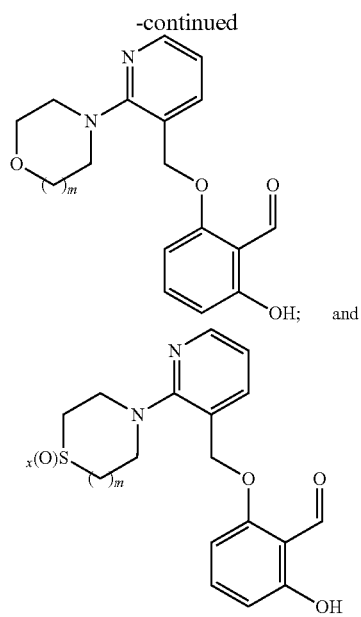

or an N oxide thereof, wherein
$R^{14}$ is $C_1$-$C_6$ alkyl, $C_3$-$C_8$ cycloalkyl, $COR^{15}$ or $COOR^{15}$;
$R^{15}$ is optionally substituted $C_1$-$C_6$ alkyl, optionally substituted $C_8$-$C_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S;
x is 0, 1, or 2;
p is 0, 1, and 2; and
m is 0, 1 or 2.

In one embodiment, the compound is

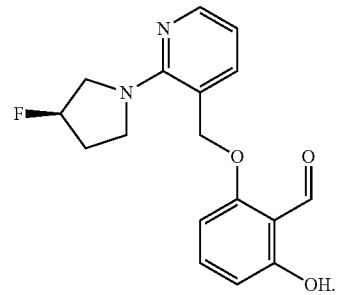 [SMILES: O=Cc1c(O)cccc1OCc1cccnc1N1CC[C@@H](F)C1]

Prodrug Moiety

In one aspect, R is hydrogen, a phosphate or a diphosphate containing moiety, or another promoiety or prodrug moiety. Preferably the prodrug moiety imparts at least a 2 fold, more preferably a 4 fold, enhanced solubility and/or bioavailability to the active moiety (where R is hydrogen), and more preferably is hydrolyzed in vivo. The promoieties are structurally and functionally defined herein.

In one embodiment, R is —$COR^{90}$, $CO_2R^{91}$, or $CONR^{92}R^{93}$ wherein
$R^{90}$ and $R^{91}$ independently are $C_1$-$C_6$ alkyl, $C_3$-$C_8$ cycloalkyl, 4-9 membered heterocycle, or a 5-10 membered heteroaryl, each containing at least 1 basic nitrogen moiety; and $R^{92}$ and $R^{93}$ independently are $C_1$-$C_6$ alkyl; $C_3$-$C_8$ cycloalkyl, 4-9 membered heterocycle, or a 5-10 membered heteroaryl, each containing at least 1 basic nitrogen moiety; or $R^{92}$ and $R^{93}$ together with the nitrogen atom they are bonded to for a 4-9 member heterocycle substituted with at least 1 amino, $C_1$-$C_6$ alkyl amino, or di $C_1$-$C_6$ alkylamino group.

In certain embodiments, R is —C(O)$R^{31}$, C(O)O$R^{31}$, or CON($R^{13}$)$_2$, each $R^{31}$ is independently a $C_1$-$C_6$ alkyl; $C_3$-$C_8$ cycloalkyl, 4-9 membered heterocycle, or a 5-10 membered heteroaryl, containing at least 1 basic nitrogen moiety; and each $R^{13}$ independently are $C_1$-$C_6$ alkyl; $C_3$-$C_8$ cycloalkyl, 4-9 membered heterocycle, or a 5-10 membered heteroaryl, containing at least 1 basic nitrogen moiety; or 2 $R^{13}$ together with the nitrogen atom they are bonded to for a 4-9 member heterocycle substituted with at least 1 amino, $C_1$-$C_6$ alkyl amino, or di $C_1$-$C_6$ alkylamino group.

Preferably, $R^1$ is isopropyl.

In one aspect, R is C(O)O$R^{31}$, C(S)O$R^{31}$, C(O)S$R^{31}$ or CO$R^{31}$, wherein $R^{31}$ is as defined herein.

In one embodiment, $R^{31}$ is a group of the formula $(CR^{32}R^{33})_e NR^{34}R^{35}$, wherein each $R^{32}$ and $R^{33}$ is independently H, a $C_1$-$C_8$ alkyl, $C_3$-$C_9$ heterocyclyl, $C_3$-$C_8$ cycloalkyl, $C_6$-$C_{10}$ aryl, $C_3$-$C_9$ heteroaryl or $R^{32}$ and $R^{33}$ together with the carbon atom they are bond to form a $C_3$-$C_8$ cycloalkyl, $C_6$-$C_{10}$ aryl, $C_3$-$C_9$ heterocyclyl or $C_3$-$C_8$ heteroaryl ring system, or 2 adjacent $R^{32}$ moieties or 2 adjacent $R^{33}$ moieties together with the carbon atom they are bond to form a $C_3$-$C_8$ cycloalkyl, $C_6$-$C_{10}$ aryl, $C_3$-$C_9$ heterocyclyl or $C_3$-$C_8$ heteroaryl ring system;

each $R^{34}$ and $R^{35}$ is a $C_1$-$C_8$ alkyl, $C_3$-$C_9$ heterocyclyl, $C_3$-$C_8$ cycloalkyl, or $R^{34}$ and $R^{35}$ together with the nitrogen atom they are bond to form a $C_3$-$C_8$ cycloalkyl or $C_3$-$C_9$ heterocyclyl ring system;

each heterocyclic and heteroaryl ring system is optionally substituted with $C_1$-$C_3$ alkyl, —OH, amino and carboxyl groups; and e is an integer of from 1 to 4.

In some less preferred embodiments $R^{34}$ and $R^{35}$ can be hydrogen.

In one embodiment, the subscript e is preferably 2 and each $R^{32}$ and $R^{33}$ is preferably independently selected from the group, H, CH$_3$, and a member in which $R^{32}$ and $R^{33}$ are joined together to form a cyclopropyl, cyclobutyl, cyclopentyl; cyclohexyl, or 1,1-dioxo-hexahydro-1λ$^6$-thiopyran-4-yl or tetrahydropyran-4-yl group.

With regard to the prodrug group, preferred embodiments are compounds wherein $NR^{34}R^{35}$ is morpholino.

In one embodiment, R is:

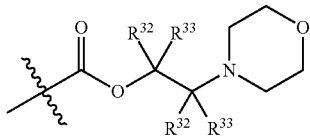

wherein
each $R^{32}$ and $R^{33}$ is independently H, $C_1$-$C_8$ alkyl, or optionally, if both present on the same substituent, may be joined together to form a $C_3$-$C_8$ cycloalkyl, $C_6$-$C_{10}$ aryl, $C_3$-$C_9$ heterocyclyl or $C_3$-$C_9$ heteroaryl ring system.

Within this embodiment, each $R^{32}$ and $R^{33}$ is independently, H, CH$_3$, or are joined together to form a cyclopropyl, cyclopbutyl, cyclopentyl, cyclohexyl, 1,1-dioxo-hexahydro-1λ$^6$-thiopyran-4-yl or tetrahydropyran-4-yl group.

In a preferred embodiment, linkage of the prodrug moiety to the rest of the active molecule is stable enough so that the serum half life of the prodrug is from about 8 to about 24 hours.

In an embodiment of the invention, the prodrug moiety comprises a tertiary amine having a pKa near the physiological pH of 7.5. Any amines having a pKa within 1 unit of 7.5 are suitable alternatives amines for this purpose. The amine may be provided by the amine of a morpholino group. This pKa range of 6.5 to 8.5 allows for significant concentrations of the basic neutral amine to be present in the mildly alkaline small intestine. The basic, neutral form of the amine prodrug is lipophilic and is absorbed through the wall of the small intestine into the blood. Following absorption into the bloodstream, the prodrug moiety is cleaved by esterases which are naturally present in the serum to release an active compound.

Examples of R include, without limitation:

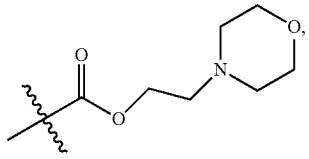

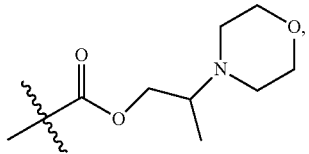

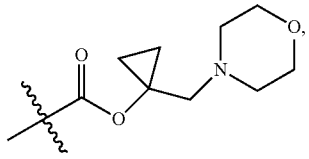

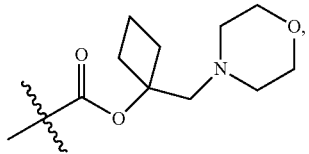

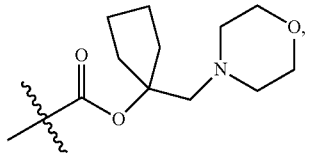

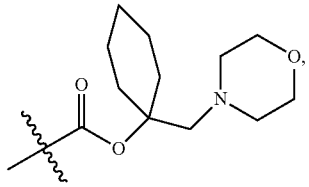

-continued

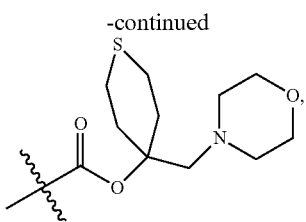

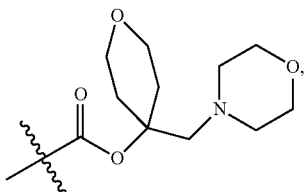

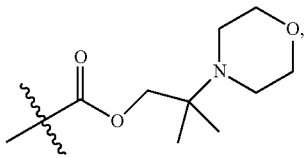

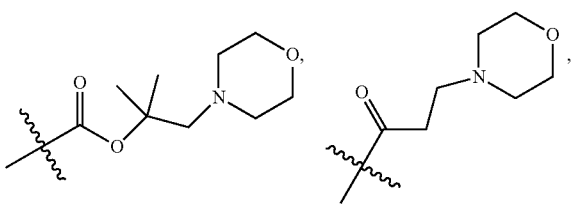

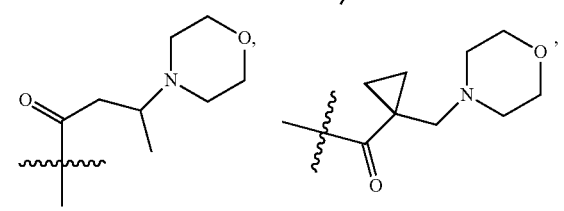

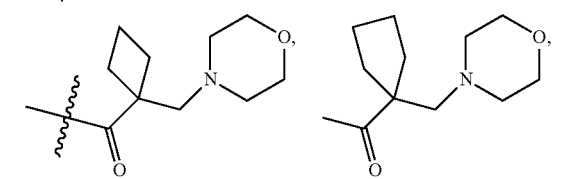

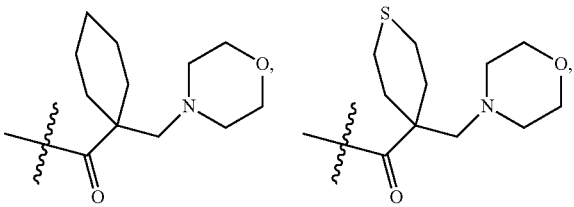

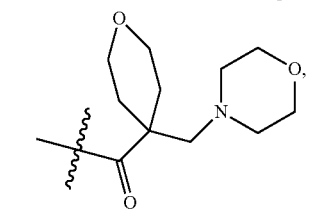

-continued

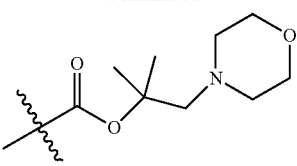

In another embodiment, R is as tabulated below:

| R | $R^1$ | m | $R^{34}$ | $R^{35}$ | $NR^{34}R^{35}$ |
|---|---|---|---|---|---|
| $C(O)(CH_2)_m NR^{34}R^{35}$ | isopropyl | 2 | Me | Me | |
| $C(O)(CH_2)_m NR^{34}R^{35}$ | isopropyl | 3 | Me | Me | |
| $C(O)(CH_2)_m NR^{34}R^{35}$ | isopropyl | 4 | Me | Me | |
| $C(O)(CH_2)_m NR^{34}R^{35}$ | isopropyl | 2 | | | morpholine |
| $C(O)(CH_2)_m NR^{34}R^{35}$ | isopropyl | 3 | | | morpholine |
| $C(O)(CH_2)_m NR^{34}R^{35}$ | isopropyl | 4 | | | morpholine |
| $C(O)O(CH_2)_m NR^{34}R^{35}$ | isopropyl | 2 | Me | Me | |
| $C(O)O(CH_2)_m NR^{34}R^{35}$ | isopropyl | 3 | Me | Me | |
| $C(O)O(CH_2)_m NR^{34}R^{35}$ | isopropyl | 4 | Me | Me | |
| $C(O)O(CH_2)_m NR^{34}R^{35}$ | isopropyl | 2 | | | morpholine |
| $C(O)O(CH_2)_m NR^{34}R^{35}$ | isopropyl | 3 | | | morpholine |
| $C(O)O(CH_2)_m NR^{34}R^{35}$ | isopropyl | 4 | | | morpholine |
| $P(O)(OH)_2$ | isopropyl | | | | | an N oxide thereof, or a pharmaceutically acceptable salt of each thereof.

In another aspect, R is,

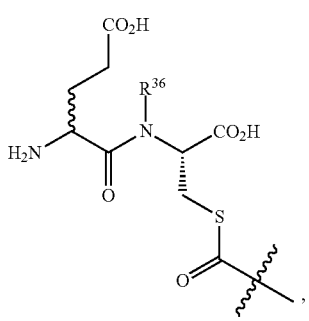

-continued

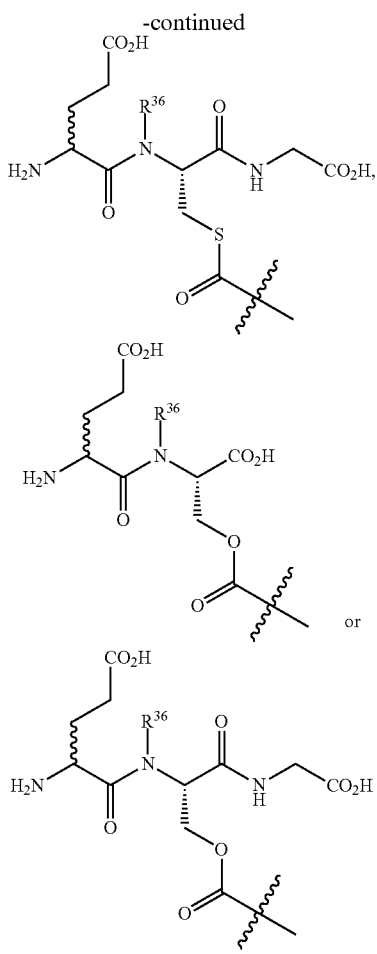

or wherein
$R^{36}$ is lower alkyl (e.g. $C_1$-$C_6$ alkyl).
In yet another aspect, R is:

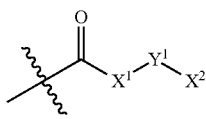

wherein $X^1$, $V^1$ and $X^2$ are as defined herein.

In one embodiment, $X^1$ is selected from the group consisting of O, S and $NR^{37}$ wherein $R^{37}$ is hydrogen or $C_1$-$C_6$ alkyl;

$Y^1$ is $-C(R^{38})_2$ or a sugar moiety, wherein each $R^{38}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl;

$X^2$ is selected from the group consisting of halogen, $C_1$-$C_6$ alkoxy, diacylglycerol, amino, $C_1$-$C_6$ alkylamino, $C_1$-$C_6$ dialkylamino, $C_1$-$C_6$ alkylthio, a PEG moiety, a bile acid moiety, a sugar moiety, an amino acid moiety, a di- or tri-peptide, a PEG carboxylic acid, and —U—V wherein
U is O or S; and
V is selected from the group consisting of $C_1$-$C_6$ alkyl, $C_3$-$C_8$ cycloalkyl, $C_3$-$C_9$ heterocyclyl, $C_6$-$C_{10}$ aryl, $C_3$-$C_9$ heteroaryl, $C(W^2)X^3$, $PO(X^3)_2$, and $SO_2X^3$;
wherein $W^2$ is O or $NR^{39}$
wherein $R^{39}$ is hydrogen or $C_1$-$C_6$ alkyl, $C_3$-$C_8$ cycloalkyl, $C_3$-$C_9$ hetrocyclyl, $C_6$-$C_{10}$ aryl, or $C_3$-$C_9$ heteroaryl; and
each $X^3$ is independently amino, hydroxyl, mercapto, $C_1$-$C_6$ alkyl, heteroalkyl, cycloalkyl, hetrocyclyl, aryl, or heteroaryl, $C_1$-$C_6$ alkoxy, $C_1$-$C_6$ alkylamino, $C_1$-$C_6$ dialkylamino, $C_1$-$C_6$ alkylthio, a bile acid based alkoxy group, a sugar moiety, a PEG moiety, and $-O-CH_2-CH(OR^{40})CH_2X^4R^{40}$,
wherein:
$X^4$ is selected from the group consisting of O, S, S=O, and $SO_2$; and
each $R^{40}$ is independently $C_{10}$-$C_{22}$ alkyl, $C_3$-$C_8$ cycloalkyl, $C_3$-$C_9$ heterocyclyl, $C_6$-$C_{10}$ aryl, or $C_3$-$C_9$ heteroaryl, $C_1$-$C_8$ alkylene, or $C_1$-$C_8$ heteroalkylene.

Each heterocyclic and heteroaryl ring system is optionally substituted with $C_1$-$C_3$ alkyl, —OH, amino and carboxyl groups.

In one embodiment, the present invention utilizes the following $Y^1$ groups: $CH_2$, CHMe, CH(isopropyl), CH(tertiarybutyl), $C(Me)_2$, $C(Et)_2$, $C(isopropyl)_2$, and $C(propyl)_2$.

In another embodiment, the present invention utilizes the following $X^2$ groups:

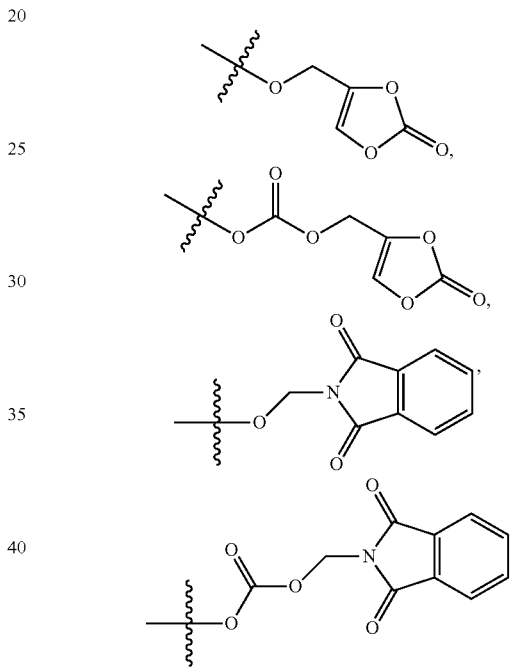

—OMe, —OEt, —O-isopropyl, O-isobutyl, O-tertiarybutyl, —O—COMe, —O—C(=O)(isopropyl), —O—C(O)(isobutyl), —O—C(=O)(tertiarybutyl), —O—C(=O)—$NMe_2$, —O—C(=O)—NHMe, —O—C(=O)—$NH_2$, —O—C(=O)—N(H)—CH($R^{41}$)—$CO_2Et$ wherein $R^{41}$ is a side chain $C_1$-$C_6$ alkyl, or $C_3$-$C_9$ heterocyclyl group selected from the side chain groups present in essential amino acids; —O—P(=O)(OMe)$_2$, —O—P(=O)(O-isopropyl)$_2$, and —O—P(=O)(O-isobutyl)$_2$. Each heterocyclic is optionally substituted with one or more, preferably, 1-3, $C_1$-$C_3$ alkyl, —OH, amino and/or carboxyl groups.

In another embodiment, In one embodiment, R is:

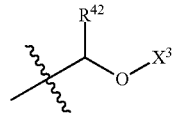

wherein
$X^3$ is independently $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl; and $R^{42}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Each heterocyclic is optionally substituted with one or more, preferably, 1-3, $C_1$-$C_3$ alkyl, —OH, amino and/or carboxyl groups.

In one embodiment, R is:

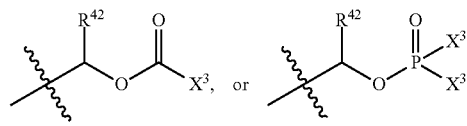

wherein each $X^3$ is independently amino, hydroxyl, mercapto, $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl, $C_1$-$C_6$ alkoxy, $C_1$-$C_6$ alkylamino, $C_1$-$C_6$ dialkylamino, $C_1$-$C_6$ alkylthio, a bile acid based alkoxy group, a sugar moiety, a PEG moiety, and —O—$CH_2$—CH($OR^{40}$)$CH_2X^4R^{40}$, wherein:

$X^4$ is selected from the group consisting of O, S, S=O, and $SO_2$; and each $R^{40}$ is independently $C_{10}$-$C_{22}$ alkyl, $C_3$-$C_8$ cycloalkyl, $C_3$-$C_9$ heterocyclyl, $C_6$-$C_{10}$ aryl, $C_3$-$C_9$ heteroaryl, $C_1$-$C_8$ alkylene, or $C_1$-$C_8$ heteroalkylene; and $R^{42}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

In some embodiments, $R^{42}$ is independently hydrogen or $C_1$-$C_6$ alkyl, $C_3$-$C_8$ cycloalkyl, $C_3$-$C_8$ heterocyclyl, $C_6$-$C_{10}$ aryl, or $C_3$-$C_8$ heteroaryl; and each $X^3$ independently is $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl, $C_1$-$C_6$ alkoxy, $C_1$-$C_6$ alkylamino, $C_1$-$C_6$ dialkylamino, or $C_1$-$C_6$ alkylthio.

In some embodiments, R is represented by the following structures:

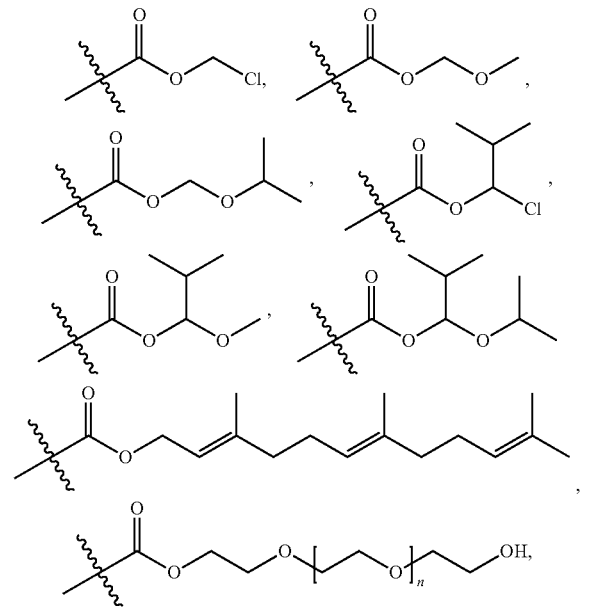

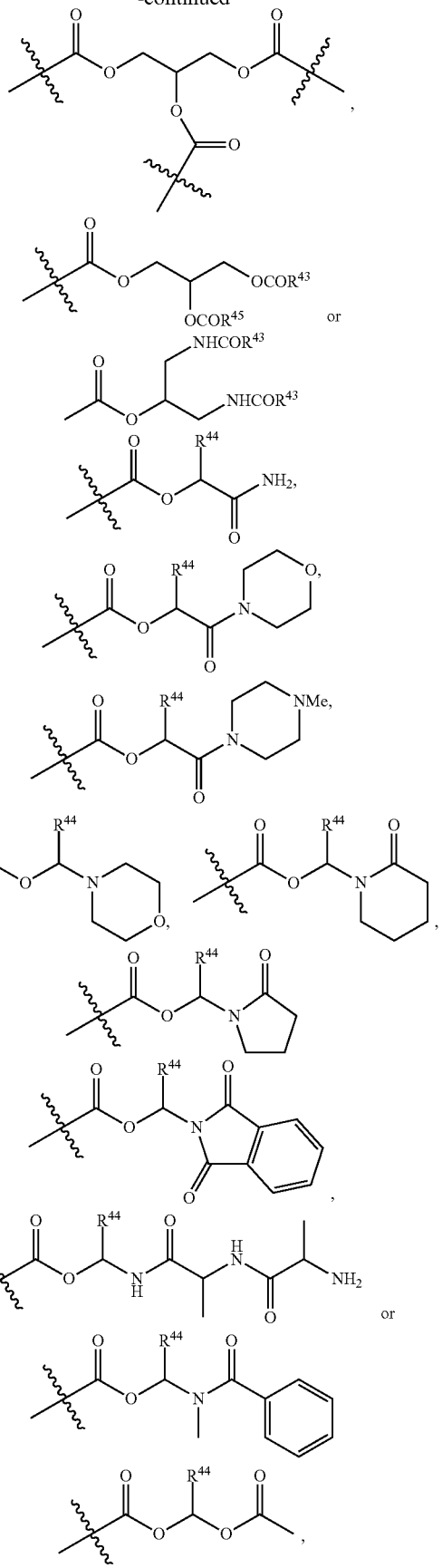

-continued

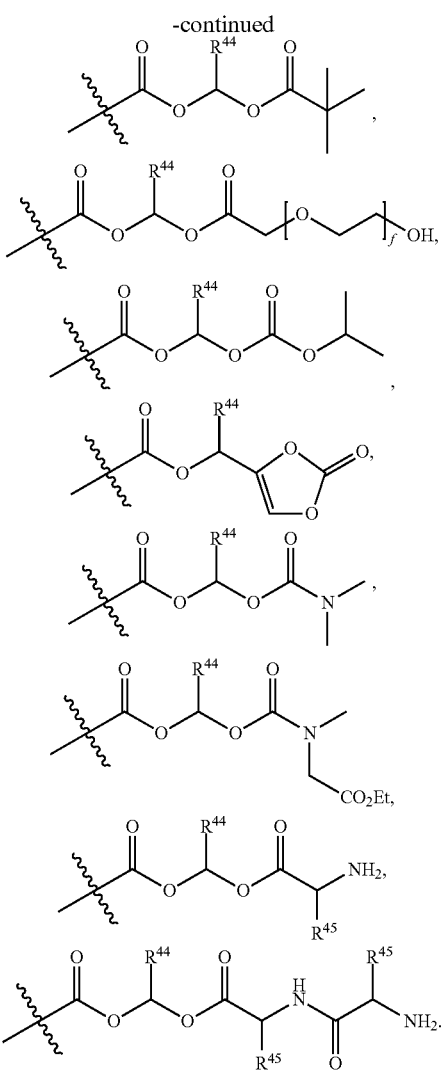

wherein, in the above examples, $R^{43}$ is $C_{10}$-$C_{22}$ alkyl or alkylene, $R^{44}$ is H or $C_1$-$C_6$ alkyl and $R^{45}$ represents side chain alkyl groups present in naturally occurring alpha amino acids;

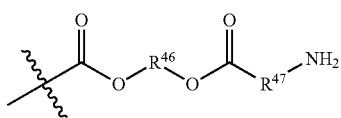

wherein $R^{46}$ is $(CH_2)_n$, f=2-4, and CO—$R^{47}$—$NH_2$ represents an aminoacyl group; or

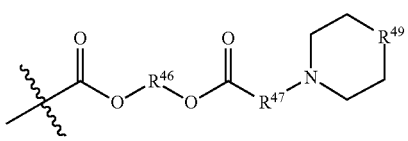

wherein $R^{46}$ is $(CH_2)_n$ n=2-4, $R^{47}$ is $(CH_2)_n$, n=1-3 and $R^{49}$ is O or NMe.

In one embodiment, R is:

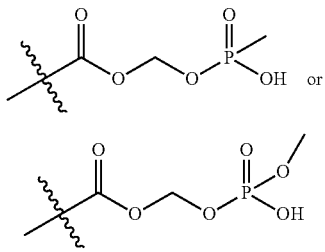

In one aspect, R is —$C(R^{200}R^{201})O(R^{202}R^{203})P(O)$ $OR^{204}NR^{205}R^{206}$, wherein each $R^{200}$, $R^{201}$, $R^{202}$, $R^{203}$, $R^{204}R^{205}$ and $R^{206}$ is independently H, a $C_1$-$C_8$ alkyl, $C_3$-$C_9$ heterocyclyl, $C_3$-$C_8$ cycloalkyl, $C_6$-$C_{10}$ aryl, $C_3$-$C_9$ heteroaryl, wherein each alkyl, heterocyclyl, cycloalkyl, aryl, and heteroaryl is optionally substituted.

In some embodiments, R is —$CH(R^{201})OCH_2P(O)$ $OR^{204}NHR^{206}$, wherein $R^{201}$ is $C_1$-$C_8$ alkyl, $R^{204}$ is phenyl, optionally substituted. In one embodiment, $R^{206}$ is —$CHR^{207}C(O)OR^{208}$ wherein $R^{207}$ is selected from the group consisting of the naturally occurring amino acid side chains and $CO_2H$ esters thereof and $R^{208}$ is $C_1$-$C_8$ alkyl. In one embodiment, $R^{206}$ is $C_1$-$C_6$ alkyl, optionally substituted with 1-3, $CO_2H$, SH, $NH_2$, $C_6$-$C_{10}$ aryl, and $C_2$-$C_{10}$ heteroaryl.

In some embodiments, R is:

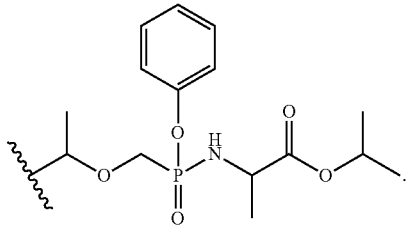 [SMILES: *C(C)OCP(=O)(NC(C)C(=O)OC(C)C)Oc1ccccc1]

In one embodiment, R is:

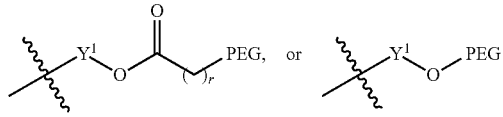

r = 0 to 12 wherein $Y^1$ is —$C(R^{38})_2$, wherein each $R^{38}$ is independently hydrogen or $C_1$-$C_6$ alkyl, $C_3$-$C_8$ cycloalkyl, $C_3$-$C_9$ heterocyclyl, $C_6$-$C_{10}$ aryl, or $C_3$-$C_9$ heteroaryl.

Various polyethylene glycol (PEG) moieties and synthetic methods related to them that can be used or adapted to make compounds of the invention are described in U.S. Pat. Nos. 6,608,076; 6,395,266; 6,194,580; 6,153,655; 6,127,355; 6,111,107; 5,965,566; 5,880,131; 5,840,900; 6,011,042 and 5,681,567.

In one embodiment, R is

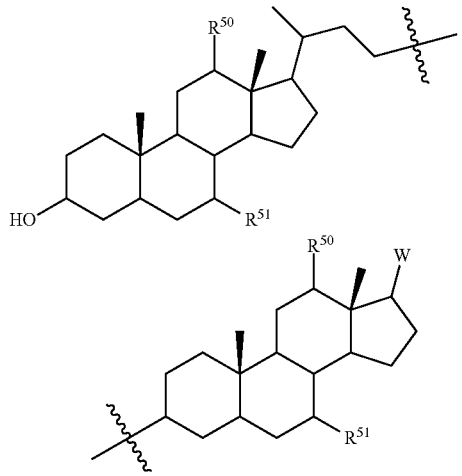

or wherein
$R^{50}$ is —OH or hydrogen;
$R^{51}$ is —OH, or hydrogen;
W is —CH(CH$_3$)W$^1$;
wherein W$^1$ is a substituted $C_1$-$C_8$ alkyl group containing a moiety which is optionally negatively charged at physiological pH,
said moiety is selected from the group consisting of $CO_2H$, $SO_3H$, $SO_2H$, —P(O)(OR$^{52}$)(OH), —OP(O)(OR$^{52}$)(OH), and $OSO_3H$,
wherein $R^{52}$ is $C_1$-$C_6$ alkyl, $C_3$-$C_8$ cycloalkyl, $C_3$-$C_8$ heterocyclyl, $C_6$-$C_{10}$ aryl, or $C_3$-$C_8$ heteroaryl.

Each heterocyclic and heteroaryl ring system is optionally substituted with one or more, preferably 1-3, $C_1$-$C_3$ alkyl, —OH, amino and/or carboxyl groups.

In one embodiment, R is:

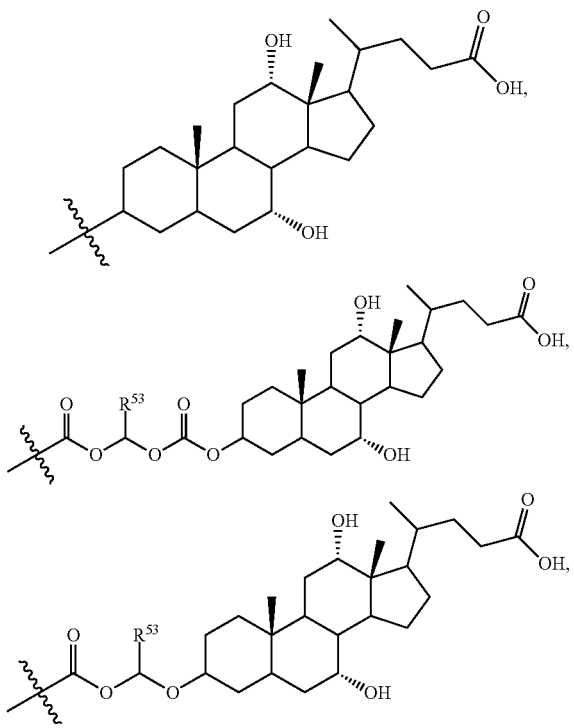

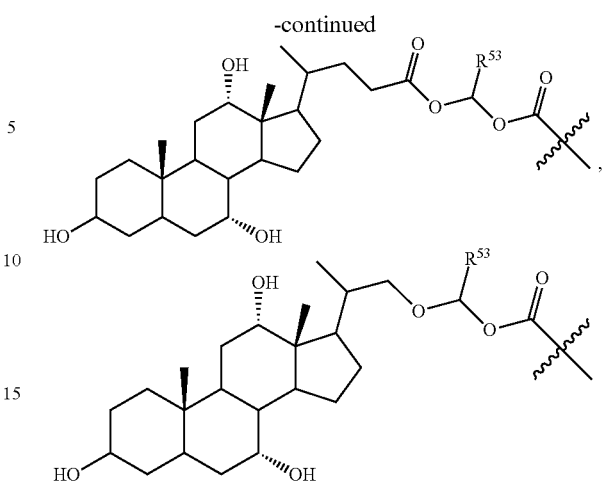

wherein $R^{53}$ is H or $C_1$-$C_6$ alkyl.

In another aspect, R is SO$_3$H.

In another aspect, R comprises a cleavable linker, wherein the term "cleavable linker" refers to a linker which has a short half life in vivo. The breakdown of the linker Z in a compound releases or generates the active compound. In one embodiment, the cleavable linker has a half life of less than ten hours. In one embodiment, the cleavable linker has a half life of less than an hour. In one embodiment, the half life of the cleavable linker is between one and fifteen minutes. In one embodiment, the cleavable linker has at least one connection with the structure: C*—C(=X*)X*—C* wherein C* is a substituted or unsubstituted methylene group, and X* is S or O. In one embodiment, the cleavable linker has at least one C*—C(=O)O—C* connection. In one embodiment, the cleavable linker has at least one C*—C(=O)S—C* connection. In one embodiment, the cleavable linker has at least one —C(=O)N*—C*—SO$_2$—N*-connection, wherein N* is —NH— or $C_1$-$C_6$ alkylamino. In one embodiment, the cleavable linker is hydrolyzed by an esterase enzyme.

In one embodiment, the linker is a self-immolating linker, such as that disclosed in U.S. patent publication 2002/0147138, to Firestone; PCT Appl. No. US05/08161 and PCT Pub. No. 2004/087075. In another embodiment, the linker is a substrate for enzymes. See generally Rooseboom et al., 2004, Pharmacol. Rev. 56:53-102.

Pharmaceutical Compositions

In further aspects of the invention, a composition is provided comprising any of the compounds described herein, and at least a pharmaceutically acceptable excipient.

In another aspect, this invention provides a composition comprising any of the compounds described herein, and a pharmaceutically acceptable excipient.

Such compositions can be formulated for different routes of administration. Although compositions suitable for oral delivery will probably be used most frequently, other routes that may be used include transdermal, intravenous, intraarterial, pulmonary, rectal, nasal, vaginal, lingual, intramuscular, intraperitoneal, intracutaneous, intracranial, and subcutaneous routes. Suitable dosage forms for administering any of the compounds described herein include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16th ed., A. Oslo editor, Easton Pa. 1980).

Pharmaceutically acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. In certain embodiments, the compositions provided herein comprises one or more of α-tocopherol, gum arabic, and/or hydroxypropyl cellulose.

In one embodiment, this invention provides sustained release formulations such as drug depots or patches comprising an effective amount of a compound provided herein. In another embodiment, the patch further comprises gum Arabic or hydroxypropyl cellulose separately or in combination, in the presence of alpha-tocopherol. Preferably, the hydroxypropyl cellulose has an average MW of from 10,000 to 100,000. In a more preferred embodiment, the hydroxypropyl cellulose has an average MW of from 5,000 to 50,000.

Compounds and pharmaceutical compositions of this invention maybe used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

Methods of Treatment

In aspects of the invention, a method is provided for increasing tissue and/or cellular oxygenation, the method comprising administering to a subject in need thereof a therapeutically effective amount of any of the compounds or compositions described herein.

In aspects of the invention, a method is provided for increasing oxygen affinity of hemoglobin S in a subject, the method comprising administering to a subject in need thereof a therapeutically effective amount of any of the compounds or compositions described herein.

In aspects of the invention, a method is provided for treating a condition associated with oxygen deficiency, the method comprising administering to a subject in need thereof a therapeutically effective amount of any of the compounds or compositions described herein.

In further aspects of the invention, a method is provided for treating oxygen deficiency associated with sickle cell anemia, the method comprising administering to a subject in need thereof a therapeutically effective amount of any of the compounds or compositions described herein.

In further aspects of the invention, a method is provided for treating sickle cell disease, the method comprising administering to a subject in need thereof a therapeutically effective amount of a compound of any of the compounds or compositions described herein. In still further aspects of the invention, a method is provided for treating cancer, a pulmonary disorder, stroke, high altitude sickness, an ulcer, a pressure sore, Alzheimer's disease, acute respiratory disease syndrome, and a wound, the method comprising administering to a subject in need thereof a therapeutically effective amount of a compound of any of the compounds or compositions described herein.

Synthetic Methods

Certain methods for making the compounds described herein are also provided. The reactions are preferably carried out in a suitable inert solvent that will be apparent to the skilled artisan upon reading this disclosure, for a sufficient period of time to ensure substantial completion of the reaction as observed by thin layer chromatography, $^1$H-NMR, etc. If needed to speed up the reaction, the reaction mixture can be heated, as is well known to the skilled artisan. The final and the intermediate compounds are purified, if necessary, by various art known methods such as crystallization, precipitation, column chromatography, and the likes, as will be apparent to the skilled artisan upon reading this disclosure.

An illustrative and non-limiting method for synthesizing a compound of formula (I), is schematically shown below.

In the following Schemes,

refer to rings A, B and C as described herein.

X and $X^5$ each represent a leaving group and are independently selected from Cl, F, Br, and I.

$X^6$ represents $CHR^{14}$, $NR^{14}$, O, $S(O)_x$; wherein x is 0, 1, or 2;

$Y^5$ represents a leaving group selected from Cl, F, Br, I, $OSO_2R^{17}$ and $OSO_2Ar$;

$R^{17}$ is $C_1$-$C_6$ alkyl;

n is 0, 1, or 2;

Ar is phenyl optionally substituted with 1-3 halo or $C_1$-$C_4$ alkyl groups.

General Synthetic Schemes

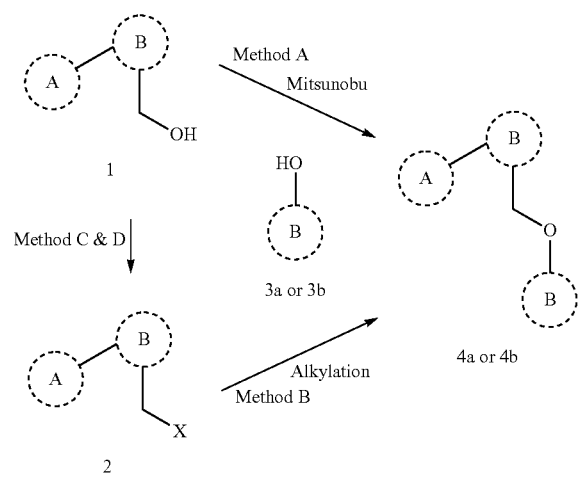

General Method A for Preparing Aryloxy Ether Analogs (4a) from Substituted Methylene Alcohol (1) and Hydroxyl Aryl Aldehyde Derivative (3a).

A hydroxyl arylaldehyde derivative (3a) (0.1-2 mmol) mixture with substituted methylene alcohol (1) (0.8 to 1.2 eq) and $PPh_3$ (1-1.5 eq) in anhydrous THF (1-10 ml) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was stirred for 10 min, then filtered through a pad of silica. The silica was washed with ethyl acetate 2-20 mL. The combined filtrates were evaporated and the residue was dried on highvac. The residue was purified by preparative HPLC or flash silica gel chromatography.

General Method B for Preparing Aryloxy Ether Analogs (4a) from Substituted Methylene Halide (2) and Hydroxyl Aryl Aldehyde Derivatives (3a).

A mixture of hydroxyl arylaldehyde derivatives (3a) (0.1-2 mmol, 1-4 eq.), substituted methylene chloride or bromide (2) (1 eq), and $K_2CO_3$ (2-5 eq.) (catalytic amount of NaI or $Bu_4NI$ may also be added) in DMF or acetonitrile (1 to 10 mL) was stirred at RT or heating up to 120° C. for 0.5-8 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous $NH_4Cl$ was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvents mixture (e.g., ethyl acetate/hexanes).

General Method C for Preparing Substituted Methylene Chloride (2a).

To a solution of substituted methylene alcohol (1) (0.1 to 2 mmol) in DCM (1-10 mL) was added $SOCl_2$ dropwise (2 eq to 5 eq) at 0° C. or RT. The reaction mixture was stirred at RT for 10 min to 6 h, or until reaction is judged complete (LC/MS). The reaction mixture is concentrated to dryness over a rotavap. The crude chloride residue was suspended in toluene, sonicated and concentrated to dryness. The process was repeated three times and dried under vacuum to give the substituted methylene chloride (2), usually as an off-white solid, which was used for next step without further purification. Alternatively, a solution of aqueous 1N $Na_2CO_3$ is then added to produce a solution of pH~8. the mixture was extracted with DCM (3×10-50 mL), dried over sodium sulfate, and concentrated to the crude substituted methylene chloride (2a), which is then purified by column chromatography on silica gel (0-100% ethyl acetate-hexanes).

General Method D for Preparing Substituted Methylene Bromide (2b).

To a solution of substituted methylene alcohol (1) (0.1 to 2 mmol) in DCM (1-10 mL) was added $Ph_3PBr_2$ dropwise (2 eq to 5 eq) at 0° C. or RT. The reaction mixture was stirred at RT for 10 min to 2 h, or until reaction is judged complete (LC/MS). The reaction mixture is concentrated to dryness over a rotavap. The residue purified by column chromatography on silica gel (0-100% ethyl acetate-hexanes) to afford the pure bromide 2b.

Similarly, N-linked heterocyclic analogs (compound 5) can also be synthesized from amination procedures developed by Buchwald and Hartwig.

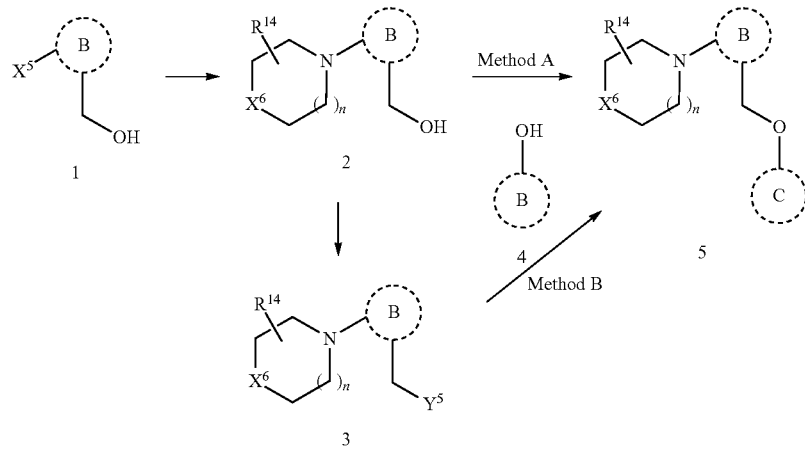

Protected amides of formula —CONHR$^{95}$ and —CONHOR$^{95}$ can be converted e.g., hydrolyzed to the corresponding amides according to methods known to the skilled artisan.

Prodrug Synthesis

Syntheses of the ester prodrugs start with the free carboxylic acid bearing the tertiary amine. The free acid is activated for ester formation in an aprotic solvent and then reacted with a free alcohol group in the presence of an inert base, such as triethyl amine, to provide the ester prodrug. Activating conditions for the carboxylic acid include forming the acid chloride using oxalyl chloride or thionyl chloride in an aprotic solvent, optionally with a catalytic amount of dimethyl formamide, followed by evaporation. Examples of aprotic solvents, include, but are not limited to methylene chloride, tetrahydrofuran, and the like. Alternatively, activations can be performed in situ by using reagents such as BOP (benzotriazol-1-yloxytris(dimethylamino) phosphonium hexafluorophosphate, and the like (see Nagy et al., 1993, Proc. Natl. Acad. Sci. USA 90:6373-6376) followed by reaction with the free alcohol. Isolation of the ester products can be affected by extraction with an organic solvent, such as ethyl acetate or methylene chloride, against a mildly acidic aqueous solution; followed by base treatment of the acidic aqueous phase so as to render it basic; followed by extraction with an organic solvent, for example ethyl acetate or methylene chloride; evaporation of the organic solvent layer; and recrystallization from a solvent, such as ethanol. Optionally, the solvent can be acidified with an acid, such as HCl or acetic acid to provide a pharmaceutically acceptable salt thereof. Alternatively the crude reaction can be passed over an ion exchange column bearing sulfonic acid groups in the protonated form, washed with deionized water, and eluted with aqueous ammonia; followed by evaporation.

Suitable free acids bearing the tertiary amine are commercially available, such as 2-(N-morpholino)-propionic acid, N,N-dimethyl-beta-alanine, and the like. Non-commercial acids can be synthesized in straightforward manner via standard literature procedures.

Carbonate and carbamate prodrugs can be prepared in an analogous way. For example, amino alcohols and diamines can be activated using activating agents such as phosgene or carbonyl diimidazole, to provide an activated carbonates, which in turn can react with the alcohol and/or the phenolic hydroxy group on the compounds utilized herein to provide carbonate and carbamate prodrugs.

Various protecting groups and synthetic methods related to them that can be used or adapted to make compounds of the invention can be adapted from the references Testa et al., Hydrolysis in Drug and Prodrug Metabolism, June 2003, Wiley-VCH, Zurich, 419-534 and Beaumont et al., Curr. Drug Metab. 2003, 4:461-85.

Provided herein is a method of synthesizing an acyloxymethyl version of a prodrug by adapting a method from the reference Sobolev et al., 2002, J. Org. Chem. 67:401-410.

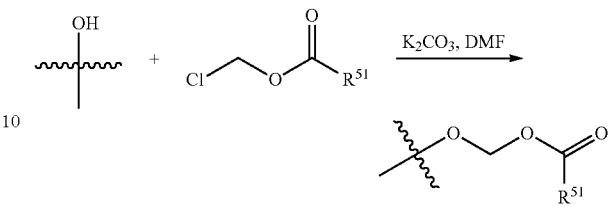

R$^{51}$ is C$_1$-C$_6$ alkyl.

Provided herein is a method for synthesizing a phosphonooxymethyl version of a prodrug by adapting a method from Mantyla et al., 2004, J. Med. Chem. 47:188-195.

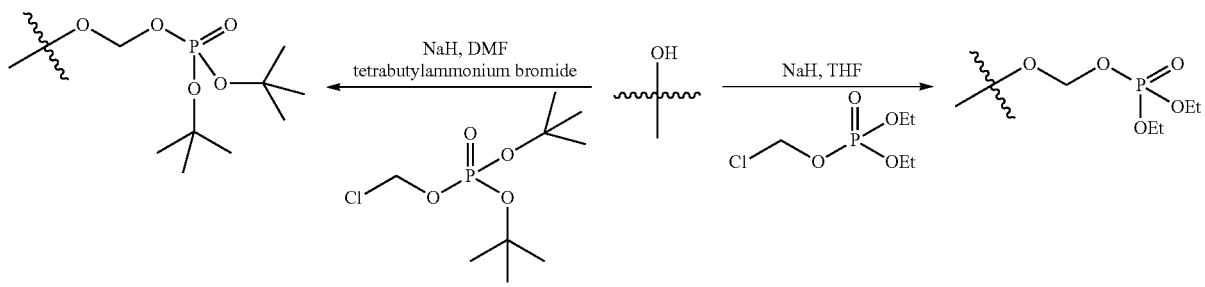

Provided herein is a method of synthesizing an alkyloxymethyl version of a prodrug

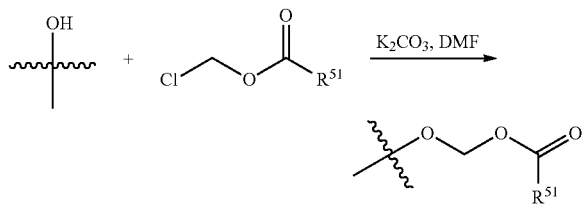

R$^{52}$ is C$_1$-C$_6$ alkyl, C$_3$-C$_8$ cycloalkyl, C$_3$-C$_9$ heterocyclyl, C$_6$-C$_{10}$ aryl, or C$_3$-C$_9$ heteroaryl.

Examples

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

In the examples below as well as throughout the application, the following abbreviations have the following meanings. If not defined, the terms have their generally accepted meanings.

° C.=degrees Celsius
RT=Room temperature
min=minute(s)

h=hour(s)
μL=Microliter
mL=Milliliter
mmol=Millimole
eq=Equivalent
mg=Milligram
MS=Mass spectrometry
LC-MS=Liquid chromatography-mass spectrometry
HPLC=High performance liquid chromatography
NMR=Nuclear magnetic resonance
EtOAc=Ethyl acetate
Ph₃PBr₂=Triphenylphosphine dibromide
DMF=N,N-Dimethylformamide
DCM=Dichloromethane
DMSO=Dimethyl sulfoxide
THF=Tetrahydrofuran
DIAD=Diisopropyl azodicarboxylate
DEAD=Diethyl azodicarboxylate Preparation of 2-[[2-[(3R)-3-fluoropyrrolidin-1-yl]pyridin-3-yl]methoxy]-6-hydroxybenzaldehyde

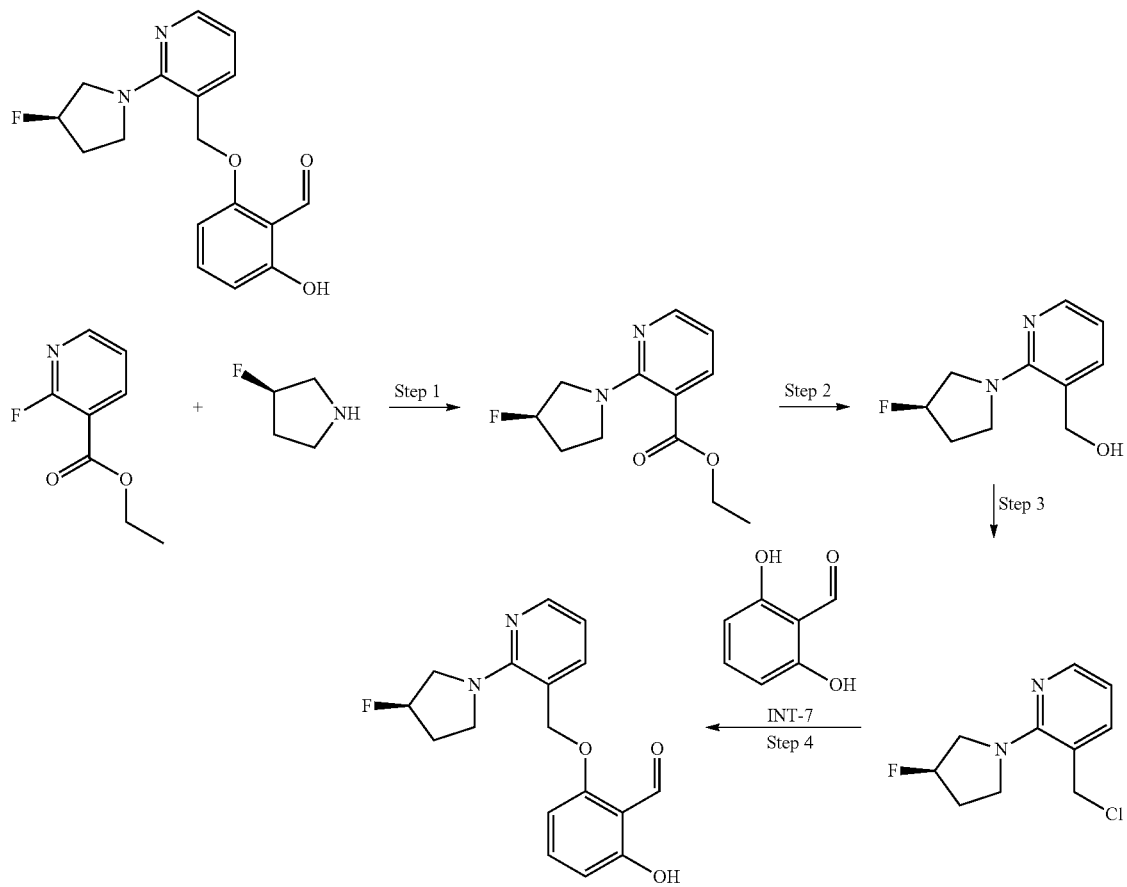

Step 1: (R)-ethyl 2-(3-fluoropyrrolidin-1-yl)nicotinate

To a solution of ethyl 2-fluoronicotinate (0.074 g, 0.48 mmol) in DMF (0.3 mL) was added diisopropylethyl amine (0.25 mL, 1.4 mmol), and (R)-3-fluoropyrrolidine (0.090 g, 0.72 mmol). The resulting mixture was irradiated with microwaves (100° C.) for 1 h and loaded directly onto a silica column. Eluting the column with EtOAc/hexanes (0-100%) provided (R)-ethyl 2-(3-fluoropyrrolidin-1-yl)nicotinate as a clear oil (0.100 g, 94% yield); MS (ESI) m/z 239 [M+H]⁺.

Step 2: (R)-(2-(3-fluoropyrrolidin-1-yl)pyridin-3-yl)methanol

To a cooled (0° C.) solution of (R)-methyl 2-(3-fluoropyrrolidin-1-yl)nicotinate in THF (5 mL) was added a solution of lithium aluminum hydride (1M in THF). The reaction mixture was stirred for 1 h and then 20 μL of H₂O was added followed by 20 μL of 15% NaOH (aq) and then 60 μL of additional water. The slurry was stirred for 1 h and filtered and the resulting residue was washed with ether. The combined organic layers were dried over MgSO₄ and concentrated in vacuo. Purification by column chromotography (EtOAc/hexanes, 0-100%) provided (R)-(2-(3-fluoropyrrolidin-1-yl)pyridin-3-yl)methanol (0.081 g, 92% yield). MS (ESI) m/z 197 [M+H]⁺.

Step 3: (R)-3-(chloromethyl)-2-(3-fluoropyrrolidin-1-yl)pyridine

To a cooled (0° C.) solution of (R)-(2-(3-fluoropyrrolidin-1-yl)pyridin-3-yl)methanol (0.081 g, 0.38 mmol) in dichloromethane was added SOCl₂ (0.450 g, 3.8 mmol) and the reaction mixture was allowed to warm to ambient temperature. After 1 h, the reaction mixture was concentrated and azeotroped with toluene to provide (R)-3-(chloromethyl)-2-(3-fluoropyrrolidin-1-yl)pyridine (0.080 g, 92%) as a clear oil. MS (ESI) m/z 215 [M+H]+.

Step 4: (R)-2-((2-(3-fluoropyrrolidin-1-yl)pyridin-3-yl)methoxy)-6-hydroxybenzaldehyde To a solution of (R)-3-(chloromethyl)-2-(3-fluoropyrrolidin-1-yl)pyridine (0.080 g, 0.35 mmol) and 2,6-dihydroxybenzaldehyde (0.130 g, 0.94 mmol) in DMF was added potassium carbonate (0.190 g, 1.4 mmol) and the reaction mixture was heated (60° C.). After 30 minutes, the DMF was removed and the resulting residue was reconstituted in CH$_2$Cl$_2$ and filtered through a plug of silica (EtOAc/hexanes, 1:1). Purification Prep-HPLC provided (R)-2-((2-(3-fluoropyrrolidin-1-yl)pyridin-3-yl)methoxy)-6-hydroxybenzaldehyde (8 mg, 5% yield). $^1$H NMR (400 MHz, DMSO-d$_6$) δ 11.71 (dd, J=8.4, 0.7 Hz, 1H), 10.21 (d, J=0.5 Hz, 1H), 8.10 (dd, J=4.8, 1.9 Hz, 1H), 7.71 (dd, J=7.4, 1.9 Hz, 1H), 7.52 (t, J=8.4 Hz, 1H), 6.73 (dd, J=8.6, 0.7 Hz, 1H), 6.71 (dd, J=7.4, 5.0 Hz, 1H), 6.53 (dt, J=8.4, 0.7 Hz, 1H), 5.40 (dd, J=54.2, 3.3 Hz, 1H), 5.28 (d, J=11.3 Hz, 1H), 5.17 (d, J=12.0 Hz, 1H), 3.91-3.56 (m, 4H), 2.21-1.93 (m, 2H); MS (ESI) m/z 317 [M+H]+.

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entirety.

The invention claimed is:

1. A compound selected from the group consisting of

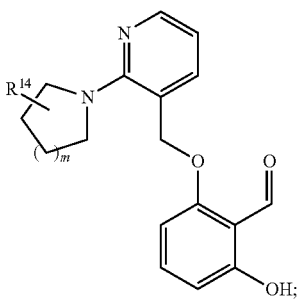

-continued

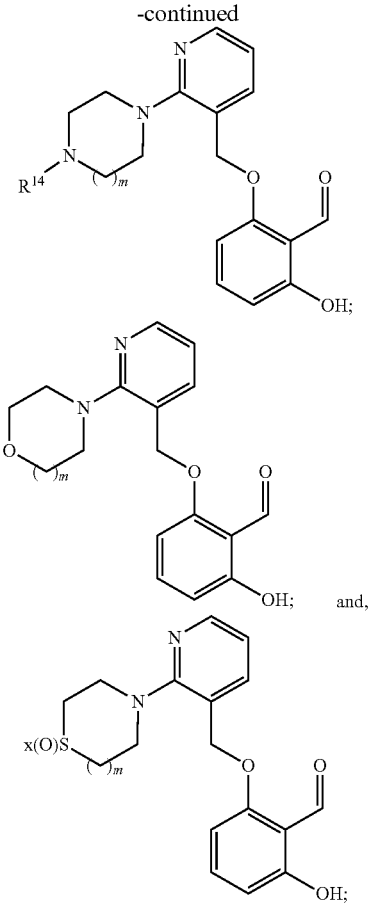

or an N oxide thereof, wherein,
R$^{14}$ is C$_1$-C$_6$ alkyl, C$_3$-C$_8$ cycloalkyl, COR$^{15}$ or COOR$^{15}$;
R$^{15}$ is optionally substituted C$_1$-C$_6$ alkyl, optionally substituted C$_6$-C$_{10}$ aryl, optionally substituted 5-10 membered heteroaryl containing up to 5 ring heteroatoms, or optionally substituted 4-10 membered heterocycle containing up to 5 ring heteroatoms, wherein the heteroatom is selected from the group consisting of O, N, S, and oxidized forms of N and S;
x is 0, 1, or 2; and
m is 0, 1 or 2.

2. A composition comprising a compound of claim 1 and at least one pharmaceutically acceptable excipient.

3. A method for increasing oxygen affinity of hemoglobin S in a subject, the method comprising administering to a subject in need thereof a therapeutically effective amount of a compound of claim 1.

* * * * *